US012601738B2

(12) United States Patent
Vandormael et al.

(10) Patent No.: US 12,601,738 B2
(45) Date of Patent: Apr. 14, 2026

(54) METHOD AND MEANS FOR DIAGNOSIS OF SPONDYLOARTHRITIS

(71) Applicants: UNIVERSITEIT HASSELT, Hasselt Limburg (BE); KATHOLIEKE UNIVERSITEIT LEUVEN, K.U. LEUVEN R&D, Leuven (BE)

(72) Inventors: Patrick Vandormael, Stevoort (BE); Veerle Somers, Sint-Truiden (BE); Kurt De Vlam, Sint Martens Leerne (BE); Dana Quaden, Diepenbeek (BE)

(73) Assignees: Universiteit Hasselt, Hasselt Limburg (BE); Katholieke Universiteit Leuven, Leuven (BE)

( * ) Notice: Subject to any disclaimer, the term of this patent is extended or adjusted under 35 U.S.C. 154(b) by 1063 days.

(21) Appl. No.: 17/761,527

(22) PCT Filed: Sep. 18, 2020

(86) PCT No.: PCT/EP2020/076120
§ 371 (c)(1),
(2) Date: Mar. 17, 2022

(87) PCT Pub. No.: WO2021/053152
PCT Pub. Date: Mar. 25, 2021

(65) Prior Publication Data
US 2022/0365082 A1     Nov. 17, 2022

(30) Foreign Application Priority Data

Sep. 18, 2019     (EP) ..................................... 19198081

(51) Int. Cl.
*G01N 33/543*     (2006.01)
*G01N 33/564*     (2006.01)

(52) U.S. Cl.
CPC ....... *G01N 33/564* (2013.01); *G01N 2800/10* (2013.01)

(58) Field of Classification Search
None
See application file for complete search history.

(56) References Cited

FOREIGN PATENT DOCUMENTS

WO     2017065000 A1     4/2017
WO     2018024732 A1     2/2018

OTHER PUBLICATIONS

Kuriyama et al., Monoclonal Anti-Dipeptide Antibodies Cross-React With Detyrosinated and Glutamylated Forms of Tubulins, Cell Motility and the Cytoskeleton 30: 171-182 (1995). (Year: 1995).*

Lederman et al. "A single amino acid substitution in a common African allele of the CD4 molecule ablates binding of the monoclonal antibody, OKT4" Mol Immunol. Nov. 1991;28(11): pp. 1171-1181. (Year: 1991).*

Harlow, E. and Lan D., Antibodies: A Laboratory Manual (1988) Cold Spring Harbor Laboratory Press, Cold Spring Harbor, NY, pp. 23-26. (Year: 1988).*

Colman et al. Research im Immunology, 1994; 145(1): pp. 33-36 (Year: 1994).*

Van Der Vekiens et al., Human and equine cardiovascular endocrinology: beware to compare, Cardiovascular Endocrinology 2013, vol. 2, No. 4, pp. 67-76. (Year: 2013).*

Torzewski et al., Animal Models of C-Reactive Protein, Hindawl Publishing Corporation, Mediators of Inflammation, vol. 2014, Article ID 683598, 2014, pp. 1-7. (Year: 2014).*

Liu et al., Autoantibodies in Spondyloarthritis, Focusing on Anti-CD74 autoantibodies, Frontiers in Immunology, Jan. 2019, vol. 10, Article 5, pp. 1-7. (Year: 2019).*

Hu et al., Anti-SIRT1 autoantibody is elevated in ankylosing spondylitis: a potential disease biomarker, BMC Immunology, 2018, 19: 38, pp. 1-8. (Year: 2018).*

EPO Communication, Extended European Search Report, Application No. EP19198081.2 Universiteit Hasselt, et al., Mail date Jun. 30, 2020, Munich, complete date, Dec. 19, 2019, 12 pgs.

Hu, Qiongyi et al., "Anti-SIRT1 autoantibody is elevated in ankylosing spondylitis: a potential disease biomarker." BMC Immunology, BioMed Central, Dec. 17, 2018, vol. 19, No. 1.

PCT International Preliminary Repot on Patentability with Article 34 Amendment, Application No. PCT/EP2020/076120 Universiteit Hasselt, International filing date of Sep. 18, 2020, date of mailing Jan. 5, 2022, 24 pgs.

PCT International Search Report and Written Opinion; Application No. PCT/EP2020/076120 Universiteit Hasselt, International filing date of Sep. 18, 2020, European Patent Office date of mailing Nov. 12, 2020, 11 pgs.

PCT Written Opinion of the International Preliminary Examining Authority, International Application No. PCT/EP2020/076120, Universiteit Hasselt, Date of mailing Sep. 7, 2021 10 pgs.

Quaden D, et al., AB0027 Screening for antibody reactivity in early axial spondyloarthritis identifies novel antigenic targets. Annals of the Rheumatic Diseases 2018;77:1215.

Quaden, D, et al., FRI0363 Autoantibodies to Three Novel Peptides in Early Axial Spondyloarthritis in Two Independent Cohorts. Annals of the Rheumatic Diseases 2019;78:863-864.

Quaden, D., et al., "Screening for Antibody Reactivity in Early Axial. Spondyloarthritis identifies Novel Antigenic Targets." Scientific Abstracts, Jun. 12, 2018, 1215. 1 pg.

Quaden, Dana H.F, et al. "Detection of Novel Diagnostic Antibodies in Ankylosing Spondylitis: An Overview." Autoimmunity Reviews, vol. 15, No. 8, 2016, pp. 820-832.

* cited by examiner

*Primary Examiner* — Gary Counts
(74) *Attorney, Agent, or Firm* — Patent Law Works LLP

(57)     ABSTRACT

The present invention in general relates to the field of antibody profiling in spondyloarthritis. In particular, the inventors found that antibody levels against selected peptides are raised in spondylarthritis patients, and herein provide a diagnostic method and kit comprising such peptides for use in the diagnosis of spondyloarthritis.

5 Claims, 4 Drawing Sheets
Specification includes a Sequence Listing.

—●— P + Specific peptide

—■— N + Specific peptide

—▲— P + Control peptide

—▼— N + control peptide

SEQUENCE LISTING

```
<160> NUMBER OF SEQ ID NOS: 12

<210> SEQ ID NO 1
<211> LENGTH: 11
<212> TYPE: PRT
<213> ORGANISM: Artificial Sequence
<220> FEATURE:
<223> OTHER INFORMATION: UH-axSpA-IgG.1

<400> SEQUENCE: 1

Ile Pro Gly Pro Ala Glu His Leu Gln His Gln
1               5                   10

<210> SEQ ID NO 2
<211> LENGTH: 10
<212> TYPE: PRT
<213> ORGANISM: Artificial Sequence
<220> FEATURE:
<223> OTHER INFORMATION: UH-axSpA-IgG.2

<400> SEQUENCE: 2

Trp Ala Pro Thr Ser Lys Thr Lys Asp Arg
1               5                   10

<210> SEQ ID NO 3
<211> LENGTH: 46
<212> TYPE: PRT
<213> ORGANISM: Artificial Sequence
<220> FEATURE:
<223> OTHER INFORMATION: UH-axSpA-IgG.3

<400> SEQUENCE: 3

Trp Gly Gln Ala Glu Leu Met Asn Lys Asn Gly Val Gly Gln Lys Ile
1               5                   10                  15

Leu His Pro Leu Gly Leu Pro Asn His Leu His Arg Ser Phe Cys Pro
            20                  25                  30

Trp Leu Gly Leu Asp Phe Ile Arg Ser Phe Phe Trp Gly Arg
```

-continued

```
              35                  40                  45
```

```
<210> SEQ ID NO 4
<211> LENGTH: 11
<212> TYPE: PRT
<213> ORGANISM: Artificial Sequence
<220> FEATURE:
<223> OTHER INFORMATION: UH-axSpA-IgG.4

<400> SEQUENCE: 4

Ile Pro Glu Leu Leu Leu Trp Lys Ile Gln Pro
1               5                   10

<210> SEQ ID NO 5
<211> LENGTH: 6
<212> TYPE: PRT
<213> ORGANISM: Artificial Sequence
<220> FEATURE:
<223> OTHER INFORMATION: UH-axSpA-IgG.5

<400> SEQUENCE: 5

Ile Pro Ile Ser Thr Phe
1               5

<210> SEQ ID NO 6
<211> LENGTH: 18
<212> TYPE: PRT
<213> ORGANISM: Artificial Sequence
<220> FEATURE:
<223> OTHER INFORMATION: UH-axSpA-IgG.6

<400> SEQUENCE: 6

Ile Arg Gln Arg Cys Ser Pro Pro Gln Leu Gln His Leu Gly Pro Glu
1               5                   10                  15

Gln Cys

<210> SEQ ID NO 7
<211> LENGTH: 9
<212> TYPE: PRT
<213> ORGANISM: Artificial Sequence
<220> FEATURE:
<223> OTHER INFORMATION: UH-axSpA-IgG.7

<400> SEQUENCE: 7

Trp Ala Glu Ser Tyr Phe Pro His Gln
1               5

<210> SEQ ID NO 8
<211> LENGTH: 252
<212> TYPE: PRT
<213> ORGANISM: Artificial Sequence
<220> FEATURE:
<223> OTHER INFORMATION: UH-axSpA-IgG.8

<400> SEQUENCE: 8

Ile Pro Pro Gly Glu Leu Glu Ala Leu Glu Gly Ala Thr Ser Leu Glu
1               5                   10                  15

Ala Pro Leu Ser Glu Glu Glu Tyr Arg Ala Leu Leu Glu Glu Leu Gln
            20                  25                  30

Asp Ala Arg Leu Gly Arg Gly Arg Leu Arg Ala Gly Arg Trp Pro Leu
        35                  40                  45

Phe Arg Arg Glu His Leu Ala Gly Tyr Val Gly Ser Cys Leu Pro His
    50                  55                  60

Ala Thr Ser Thr Gly Leu Thr Ser Leu Gly Phe Leu Pro Ser Arg Ser
```

-continued

```
65                  70                  75                  80

Arg Pro Gly Glu Arg Leu His Thr Ala Glu Thr Pro His Ser Gly Glu
                85                  90                  95

Leu Pro Phe Phe Pro Gly His Pro Gly Ala Ser Arg Leu Gly Gln Arg
                100                 105                 110

Pro Asp Ala Leu His Leu Pro Leu Pro Cys Gly Gly Phe Arg Gly His
            115                 120                 125

Gly Leu Ala Arg Trp Ser Cys Pro Gly Phe Gln Phe Ala Arg Cys Pro
            130                 135                 140

Gly Asp Leu Gly Ser Pro Asp Pro Ala Pro Pro Arg Thr Pro Leu Gly
145                 150                 155                 160

Ser Gly Trp Cys Lys His Thr Leu Ala Leu Cys Pro His Leu Ser Gly
                165                 170                 175

Pro Arg Leu Ser His Ser Ala Arg Ala Arg Gln Ala Val Ala Leu Gln
                180                 185                 190

Val Pro Val Leu Pro Ala Phe Pro Gln Val Gln Arg Pro Pro Arg Ser
            195                 200                 205

Leu Arg Val Gly Glu Ser Pro Phe Gln Arg Ser Arg Gly Gly Val Gly
            210                 215                 220

Lys Ile Pro Thr Cys Arg Gly Arg Leu Gly His Pro Arg Cys Arg Cys
225                 230                 235                 240

Gly Leu Ala Gly Leu Glu Gly Thr Ala Ala Ala Asn
                245                 250
```

```
<210> SEQ ID NO 9
<211> LENGTH: 11
<212> TYPE: PRT
<213> ORGANISM: Artificial Sequence
<220> FEATURE:
<223> OTHER INFORMATION: UH-axSpA-IgG.9

<400> SEQUENCE: 9

Leu Gly Ala Arg Thr Lys Ala Ala Val Ala Gln
1               5                   10

<210> SEQ ID NO 10
<211> LENGTH: 12
<212> TYPE: PRT
<213> ORGANISM: Artificial Sequence
<220> FEATURE:
<223> OTHER INFORMATION: UH-axSpA-IgG.5 extended

<400> SEQUENCE: 10

Glu Asn Ser Arg Pro Arg Ile Pro Ile Ser Thr Phe
1               5                   10

<210> SEQ ID NO 11
<211> LENGTH: 31
<212> TYPE: PRT
<213> ORGANISM: Artificial Sequence
<220> FEATURE:
<223> OTHER INFORMATION: UH-axSpA-IgG.8 - short

<400> SEQUENCE: 11

Ile Pro Pro Gly Glu Leu Glu Ala Leu Glu Gly Ala Thr Ser Leu Glu
1               5                   10                  15

Ala Pro Leu Ser Glu Glu Glu Tyr Arg Ala Leu Leu Glu Glu Leu
            20                  25                  30

<210> SEQ ID NO 12
```

```
<211> LENGTH: 16
<212> TYPE: PRT
<213> ORGANISM: Artificial Sequence
<220> FEATURE:
<223> OTHER INFORMATION: control peptide

<400> SEQUENCE: 12

Trp Thr Lys Thr Pro Asp Gly Asn Phe Gln Leu Gly Gly Thr Glu Pro
1               5                   10                  15
```

METHOD AND MEANS FOR DIAGNOSIS OF SPONDYLOARTHRITIS

CROSS REFERENCE TO RELATED APPLICATIONS

This application is a national phase entry under 35 U.S.C. § 371 of International Patent Application PCT/EP2020/076120, filed Sep. 18, 2020, designating the United States of America and published in English as International Patent Publication WO 2021/053152 on Mar. 25, 2021, which claims the benefit under Article 8 of the Patent Cooperation Treaty to European Patent Application Serial No. 19198081.2, filed Sep. 18, 2019, the entireties of which are hereby incorporated by reference.

FIELD OF THE INVENTION

The present invention in general relates to the field of antibody profiling in spondyloarthritis. In particular, the inventors found that antibody levels against selected peptides are raised in spondylarthritis patients, and herein provide a diagnostic method and kit comprising such peptides for use in the diagnosis of spondyloarthritis.

BACKGROUND TO THE INVENTION

Axial spondyloarthritis (axSpA) is a rheumatic disease mainly characterized by chronic inflammation of spinal and sacroiliac joints, which can also affect lower weight-bearing joints, entheses and extra-articular tissues, such as the eyes, intestines and skin (1). AxSpA diagnosis is classically based on the combination of clinical symptoms and in the case of radiographic AxSpA, unequivocal radiographic damage such as the presence of radiographic sacroiliitis according to the modified New York (mNY) criteria or the presence of syndesmophytes in the spine, or in the case of non-radiographic AxSA based on inflammation detected by dedicated MRI sequences. Since structural damage on X-rays appears several years after disease onset, there is a major diagnostic delay. In the absence of diagnostic criteria, classification criteria developed by the ASAS group (Assessment in SpondyloArthritis international Society) are often applied for diagnostic purposes in patients with suspect of axial and peripheral spondyloarthritis. These criteria combine physical examination, presence of sacroiliitis on imaging and laboratory tests for human leukocyte antigen (HLA)-B27 and C-reactive protein (CRP) (2, 3). However, these criteria are not meant for diagnosis and consequently perform less, with lower sensitivity and specificity, unable to distinguish axSpA patients from persons with non-specific chronic low back pain (LBP) at an early disease phase (4-6). Therefore, for many patients, axSpA diagnosis may be a clinical challenge and is often delayed by several years after the occurrence of first clinical symptoms (7, 8), which poses a problem for early treatment initiation. This underscores the importance of the discovery of new objective biomarkers to improve early axSpA diagnosis. Although involvement of the humoral immune response in axSpA has long been disregarded, antibodies against several microbial, inflammatory, structural and related rheumatic antigen targets have already been described in axSpA (9). Even though some of these (auto)antibodies and their antigenic targets demonstrate promising biomarker potential, further validation in different cohorts is mandatory to establish the true accuracy of these potential diagnostic biomarkers for axSpA.

SUMMARY OF THE INVENTION

In a first aspect, the present invention provides an in vitro method for diagnosing the presence, or for diagnosing the risk of development, or for the therapy control of spondyloarthritis in a subject, said method comprising:
a) providing a biological sample from the subject, and
b) determining autoantibody levels against one or more peptides selected from the list comprising SEQ ID No: 1, SEQ ID No: 2, SEQ ID No: 3, SEQ ID No: 4, SEQ ID No: 5, SEQ ID No: 6, SEQ ID No: 7, SEQ ID No: 8, or SEQ ID No: 9, or a fragment comprising at least 4 consecutive amino acids derived therefrom; wherein an increase in autoantibody levels against said one or more peptides or fragments thereof in said biological sample compared to a reference sample is indicative for the presence or the risk of development, or for the therapy control of spondyloarthritis.

In one aspect, the present invention provides an in vitro method for diagnosing spondyloarthritis in a subject, said method comprising:
a) providing a biological sample from the subject, and
b) determining the presence or quantity of autoantibodies against a polypeptide comprising a sequence of SEQ ID No: 8, or a fragment comprising at least 4 consecutive amino acids derived therefrom; wherein the presence or an increase in autoantibody levels against said polypeptide or fragments thereof in said biological sample compared to a reference sample is indicative for the presence of spondyloarthritis in the subject. In a further aspect, said method comprises determining the presence or quantity of autoantibodies against one or more polypeptides comprising a sequence selected from the list comprising SEQ ID No: 1, SEQ ID No: 2, SEQ ID No: 3, SEQ ID No: 4, SEQ ID No: 5, SEQ ID No: 6, SEQ ID No: 7, or SEQ ID No: 9, or a fragment comprising at least 4 consecutive amino acids derived therefrom, wherein the presence or an increase in autoantibody level against one or more of said polypeptides or fragments thereof compared to the reference sample is indicative for the presence of spondyloarthritis in the subject.

In still another embodiment, said method for diagnosing spondyloarthritis comprises determining the presence or quantity of autoantibodies against one or more polypeptides comprising a sequence of SEQ ID No: 8 and a sequence selected from SEQ ID No. 1 or SEQ ID No. 4, or a fragment comprising at least 4 consecutive amino acids derived therefrom, wherein the presence or increase in autoantibody level against one or more of said polypeptides or fragments thereof compared to the reference sample is indicative for the presence of spondyloarthritis in the subject.

In still another embodiment, said method for diagnosing spondyloarthritis comprises a) providing a biological sample from the subject, and b) determining the presence or quantity of autoantibodies against the polypeptides comprising a sequence of SEQ ID No: 8, SEQ ID No: 1 and SEQ ID No: 4, or a fragment comprising at least 4 consecutive amino acids derived therefrom; wherein the presence or an increase in autoantibody levels against said polypeptides or fragments thereof in said biological sample compared to a reference sample is indicative for the presence of spondyloarthritis in the subject.

In another aspect of the invention, an in vitro method for determining the risk of development of spondyloarthritis in a subject is provided. Said method comprises a) providing a biological sample from the subject, and b) determining the presence or quantity of autoantibodies against a polypeptide comprising a sequence of SEQ ID No: 8, or a fragment comprising at least 4 consecutive amino acids derived therefrom; wherein the presence or an increase in autoantibody levels against said polypeptide or fragments thereof in said biological sample compared to a reference sample is indicative for an increased risk of development of spondyloarthritis in the subject. In a further aspect, said method comprises determining the presence or quantity of autoantibodies against one or more polypeptides comprising a sequence selected from the list comprising SEQ ID No: 1, SEQ ID No: 2, SEQ ID No: 3, SEQ ID No: 4, SEQ ID No: 5, SEQ ID No: 6, SEQ ID No: 7, or SEQ ID No: 9, or a fragment comprising at least 4 consecutive amino acids derived therefrom, wherein the presence or an increase in autoantibody level against one or more of said polypeptides or fragments thereof compared to the reference sample is indicative for an increased risk of development of spondyloarthritis in the subject.

In still another embodiment, said method for determining the risk of development of spondyloarthritis in a subject comprises determining the presence or quantity of autoantibodies against one or more polypeptides comprising a sequence of SEQ ID No: 8 and a sequence selected from SEQ ID No. 1 or SEQ ID No. 4, or a fragment comprising at least 4 consecutive amino acids derived therefrom, wherein the presence or increase in autoantibody level against one or more of said polypeptides or fragments thereof compared to the reference sample is indicative for an increased risk of development of spondyloarthritis in the subject.

In still a further embodiment, said method for determining the risk of development of spondyloarthritis in a subject comprises:

a) providing a biological sample from the subject, and b) determining the presence or quantity of autoantibodies against the polypeptides comprising a sequence of SEQ ID No: 8, SEQ ID No: 1 and SEQ ID No: 4, or a fragment comprising at least 4 consecutive amino acids derived therefrom; wherein the presence or an increase in autoantibody levels against said polypeptides or fragments thereof in said biological sample compared to a reference sample is indicative for an increased risk of development of spondyloarthritis in the subject.

In another aspect, the present invention provides a method for evaluating the prognosis and/or disease severity of spondyloarthritis in a subject, said method comprising a) providing a biological sample from the subject, and b) determining the presence or quantity of autoantibodies against a polypeptide comprising a sequence of SEQ ID No: 8, or a fragment comprising at least 4 consecutive amino acids derived therefrom; wherein the presence or an increase in autoantibody levels against said polypeptide or fragments thereof in said biological sample compared to a reference sample is indicative for the prognosis and/or disease severity of spondyloarthritis in the subject. In a further aspect, the method further comprises determining the presence or quantity of autoantibodies against one or more polypeptides comprising a sequence selected from the list comprising SEQ ID No: 1, SEQ ID No: 2, SEQ ID No: 3, SEQ ID No: 4, SEQ ID No: 5, SEQ ID No: 6, SEQ ID No: 7, or SEQ ID No: 9, or a fragment comprising at least 4 consecutive amino acids derived therefrom, wherein the presence or an increase in autoantibody level against one or more of said polypeptides or fragments thereof compared to the reference sample is indicative for the prognosis and/or disease severity of spondyloarthritis in the subject.

In still another embodiment, said method for evaluating the prognosis and/or disease severity of spondyloarthritis in a subject comprises determining the presence or quantity of autoantibodies against one or more polypeptides comprising a sequence of SEQ ID No: 8 and a sequence selected from SEQ ID No. 1 or SEQ ID No. 4, or a fragment comprising at least 4 consecutive amino acids derived therefrom, wherein the presence or increase in autoantibody level against one or more of said polypeptides or fragments thereof compared to the reference sample is indicative for the prognosis and/or disease severity of spondyloarthritis in the subject.

In still another further embodiment, said method for evaluating the prognosis and/or disease severity of spondyloarthritis in a subject comprises a) providing a biological sample from the subject, and b) determining the presence or quantity of autoantibodies against the polypeptides comprising a sequence of SEQ ID No: 8, SEQ ID No: 1 and SEQ ID No: 4, or a fragment comprising at least 4 consecutive amino acids derived therefrom; wherein the presence or an increase in autoantibody levels against said polypeptides or fragments thereof in said biological sample compared to a reference sample is indicative for the prognosis and/or disease severity of spondyloarthritis in the subject.

In a further aspect of the invention, an in vitro method for selecting a patient for a specific therapy for spondyloarthritis or for evaluating the therapeutic treatment of spondyloarthritis in a subject is provided. Said method comprises a) providing a biological sample from the subject, and b) determining the presence or quantity of autoantibodies against a polypeptide comprising a sequence of SEQ ID No: 8, or a fragment comprising at least 4 consecutive amino acids derived therefrom; wherein the presence or an increase in autoantibody levels against said polypeptide or fragments thereof in said biological sample compared to a reference sample leads to the selection of a specific therapy or the evaluation of the therapeutic treatment of spondyloarthritis in the subject. In a further aspect, said method further comprises determining the presence or quantity of autoantibodies against one or more polypeptides comprising a sequence selected from the list comprising SEQ ID No: 1, SEQ ID No: 2, SEQ ID No: 3, SEQ ID No: 4, SEQ ID No: 5, SEQ ID No: 6, SEQ ID No: 7, or SEQ ID No: 9, or a fragment comprising at least 4 consecutive amino acids derived therefrom, wherein the presence or an increase in autoantibody level against one or more of said polypeptides or fragments thereof compared to the reference sample leads to the selection of a specific therapy or the evaluation of the therapeutic treatment of spondyloarthritis in the subject.

In a further embodiment, said method for selecting a patient for a specific therapy for spondyloarthritis or for evaluating the therapeutic treatment of spondyloarthritis in a subject comprises determining the presence or quantity of autoantibodies against one or more polypeptides comprising a sequence of SEQ ID No: 8 and a sequence selected from SEQ ID No. 1 or SEQ ID No. 4, or a fragment comprising at least 4 consecutive amino acids derived therefrom, wherein the presence or increase in autoantibody level against one or more of said polypeptides or fragments thereof compared to the reference sample leads to the selection of a specific therapy or the evaluation of the therapeutic treatment of spondyloarthritis in the subject. In still another further embodiment, said method for selecting a patient for a specific therapy for spondyloarthritis or for evaluating the therapeutic treatment of spondyloarthritis in a subject comprises a) providing a biological sample from the subject, and b) determining the presence or quantity of autoantibodies against the polypeptides comprising a sequence of SEQ ID No: 8, SEQ ID No: 1 and SEQ ID No: 4, or a fragment comprising at least 4 consecutive amino acids derived therefrom; wherein the presence or an increase in autoantibody levels against said polypeptides or fragments thereof in said biological sample compared to a reference sample leads to the selection of a specific therapy or the evaluation of the therapeutic treatment of spondyloarthritis in the subject.

In a further aspect of the invention, and in all in vitro methods of the present invention, determining autoantibody levels against peptides selected from the list comprising SEQ ID No: 1, SEQ ID No: 4, and SEQ ID No: 8, or a fragment comprising at least 4 consecutive amino acids derived therefrom can be combined with determining autoantibody levels against one or more peptides selected from the list comprising SEQ ID No: 2, SEQ ID No: 3, SEQ ID No: 5, SEQ ID No: 6, SEQ ID No: 7, or SEQ ID No: 9, or a fragment comprising at least 4 consecutive amino acids derived therefrom.

Alternatively, in any of the herein defined combinations of peptides, one or more "full-length peptides may be replaced by fragments thereof, comprising at least 4 consecutive amino acids; preferably at least 5 consecutive amino acids; even more preferably at least 6 consecutive amino acids.

In a particular embodiment, in all aspects of the present invention, IgA, IgG and/or IgM autoantibodies are detected.

In a further embodiment, in all aspects of the present invention, the subject is a human and the autoantibodies are human autoantibodies.

In still another further embodiment, in all aspects of the invention, the detection of autoantibodies is performed using an immunoassay, preferably with direct or indirect coupling of one reactant to a detectable marker substance; even more preferably wherein the detection is carried out using an ELISA, RIA, multiplex immunoassay, immunofluorescence assay, western blot, line assay, dot blot assay, or immuno microfluidics assay.

In a further embodiment and in all aspects of the invention, the biological sample is blood, tissue or body fluid, preferably selected from the list comprising hair, skin, nails, saliva, synovial liquid, blood serum, blood plasma, urine, tears, bone marrow fluid, cerebrospinal fluid, lymphatic fluid, amniotic fluid, nipple aspiration fluid, and the like; more preferably selected from blood serum or blood plasma.

As already outlined herein above, the in vitro methods and uses according to the different embodiments of the invention are for diagnosing the presence of spondyloarthritis, or for diagnosing the risk of development of spondyloarthritis, or for evaluating the prognosis and/or disease severity of spondyloarthritis, or for selecting a patient for a specific treatment of spondyloarthritis. In a further embodiment, spondyloarthritis includes axial spondyloarthritis and peripheral spondyloarthritis; preferably selected from ankylosing spondylitis, non-radiographic axial spondyloarthritis, undifferentiated spondyloarthritis, juvenile spondyloarthritis, psoriasisarthritis.

In still another embodiment, the in vitro methods described in the present invention and according to all their embodiments, are for diagnosing the presence of, or for diagnosing the risk of development of, or for selecting a therapy for a spondyloarthritis-associated disease. Said spondyloarthritis-associated disease is selected from inflammatory bowel disease, psoriasis and acute anterior uveitis.

In a further aspect, all methods and uses according to the different embodiments of the present invention further allow differentiation between spondyloarthritis and lower back pain; in particular allowing differentiation between spondyloarthritis and non-inflammatory lower back pain.

In still another aspect, the in vitro methods according to the different embodiments of the invention are for the stratification of the therapeutic regimen of a subject afflicted with spondyloarthritis, or being at risk of developing spondyloarthritis.

In a further aspect, the in vitro methods according to the different embodiments of the invention are for identifying the status of disease, in particular the activity of the disease, in a subject afflicted with spondyloarthritis.

The present invention is further also directed to the use of the in vitro method according to all its embodiments described herein, to tailor treatment to the patient's individual needs or to evaluate the therapeutic treatment of spondyloarthritis in a patient suffering therefrom.

In still another aspect, the present invention provides an isolated polypeptide comprising a sequence represented by any of SEQ ID Nos: 1-9, or a fragment comprising at least 4; preferably at least 6, consecutive amino acids derived from SEQ ID No: 1-9. In another aspect, the present invention provides an isolated polypeptide consisting essentially of a sequence represented by SEQ ID Nos: 1-9, or a fragment comprising at least 4, preferably at least 6, consecutive amino acids derived from SEQ ID Nos: 1-9.

Thus, a polypeptide selected from the list comprising SEQ ID No: 1, SEQ ID No: 2, SEQ ID No: 3, SEQ ID No: 4, SEQ ID No: 5, SEQ ID No: 6, SEQ ID No: 7, SEQ ID No: 8, or SEQ ID No: 9; or a fragment comprising at least 4, in particular at least 5, even more in particular at least 6, consecutive amino acids derived therefrom, is provided.

In a further preferred embodiment, the present invention provides an isolated polypeptide comprising a sequence represented by SEQ ID No: 8 or a fragment thereof comprising at least 4, preferably at least 6 consecutive amino acids thereof. In an even further embodiment, the present invention provides an isolated polypeptide consisting essentially of the sequence of SEQ ID NO: 8 or a fragment thereof comprising at least 4, preferably at least 6, consecutive amino acids derived from SEQ ID No: 8.

In a further embodiment, the present invention provides an isolated polypeptide comprising a sequence represented by SEQ ID No: 4 or a fragment thereof comprising at least 4, preferably at least 6 consecutive amino acids thereof. In an even further embodiment, the present invention provides an isolated polypeptide consisting essentially of the sequence of SEQ ID NO: 4 or a fragment thereof comprising at least 4, preferably at least 6, consecutive amino acids derived from SEQ ID No: 4.

In a further embodiment, the present invention provides an isolated polypeptide comprising a sequence represented by SEQ ID No: 1 or a fragment thereof comprising at least 4, preferably at least 6 consecutive amino acids thereof. In an even further embodiment, the present invention provides an isolated polypeptide consisting essentially of the sequence of SEQ ID NO: 1 or a fragment thereof comprising at least 4, preferably at least 6, consecutive amino acids derived from SEQ ID No: 1.

In a further embodiment, one or more polypeptides, or the immune reactive peptides thereof, for use in the diagnosis, risk assessment or therapy control of spondyloarthritis, are provided, wherein said one or more polypeptides comprise an epitope having a sequence selected from any one of SEQ ID No: 1 to 9, or a fragment comprising at least 4, in particular at least 5, even more in particular at least 6, consecutive amino acids derived therefrom. In still a further embodiment, said one or more polypeptides or the immune reactive peptides thereof comprise an epitope having a sequence selected from any one of SEQ ID No: 1, SEQ ID No: 4, or SEQ ID No: 8, or a fragment comprising at least 4, in particular at least 5, even more in particular at least 6, consecutive amino acids derived therefrom. In another further embodiment, said one or more polypeptides, or the immune reactive peptides thereof, preferably being in form of a pharmaceutical composition, are for use in the prophylaxis and/or treatment of spondyloarthritis, wherein said one or more polypeptides comprise an epitope having a sequence selected from any one of SEQ ID No: 1 to 9, or a fragment comprising at least 4, in particular at least 5, even more in particular at least 6 consecutive amino acids derived therefrom. In particular, said one or more polypeptides or the immune reactive peptides thereof comprise an epitope having a sequence selected from any one of SEQ ID No: 1, SEQ ID No: 4, or SEQ ID No: 8, or a fragment comprising at least 4, in particular at least 5, even more in particular at least 6, consecutive amino acids derived therefrom.

In further aspect, a composition is provided comprising one or more of the isolated polypeptides or fragments thereof as described above.

In a preferred embodiment, said composition comprises the isolated polypeptide comprising or consisting essentially of the sequence of SEQ ID No: 8 or a fragment comprising at least 4; preferably at least 6, consecutive amino acids thereof, and at least one other polypeptide comprising a sequence represented by any of SEQ ID Nos: 1-7 or 9, or a fragment comprising at least 4, preferably at least 6, consecutive amino acids therefrom. In another embodiment, said composition comprises the isolated polypeptide comprising or consisting essentially of the sequence of SEQ ID No: 8 or a fragment comprising at least 4; preferably at least 6, consecutive amino acids thereof, and at least one other polypeptide comprising a sequence represented by SEQ ID No: 1 or SEQ ID No 4, or a fragment comprising at least 4, preferably at least 6, consecutive amino acids derived therefrom. In a further aspect, a composition is provided comprising the isolated polypeptides consisting essentially of the sequences of SEQ ID Nos 1, 4 and 8, or a fragment thereof comprising at least 4, preferably at least 6, consecutive amino acids. In another embodiment, the composition comprises the isolated polypeptides comprising the sequences of SEQ ID Nos 1, 4 and 8, or a fragment thereof comprising at least 4, preferably at least 6, consecutive amino acids.

In a further aspect, the isolated polypeptides or the composition according to the present invention are for use in the diagnosis of spondyloarthritis. In another aspect, the isolated polypeptides or the composition according to the present invention are for use in determing the risk of development of spondyloarthritis in a subject. In another aspect, the isolated polypeptides or the composition according to the present invention are for use in selecting a therapy and/or for evaluating the therapy response in a subject diagnosed with spondyloarthritis. In still another aspect, the isolated polypeptides or the composition according to the present invention are for use in determining the prognosis and/or disease severity of spondyloarthritis.

The present invention also provides a diagnostic kit for performing the in vitro method according to any of the embodiments of the present invention, said kit comprising an isolated polypeptide or a composition according to any of the embodiments of the invention, and reagents for detecting antibody binding to said one or more polypeptides or fragments thereof. In a particular aspect, said kit comprises one or more peptides selected from the list comprising SEQ ID No: 1, SEQ ID No: 2, SEQ ID No: 3, SEQ ID No: 4, SEQ ID No: 5, SEQ ID No: 6, SEQ ID No: 7, SEQ ID No: 8, or SEQ ID No: 9, or a fragment comprising at least 4, in particular at least 5, even more in particular at least 6, consecutive amino acids derived therefrom; and reagents for detecting antibody binding to said one or more peptides or fragments therefrom.

In another aspect a diagnostic kit is provided for performing the in vitro method according to the present invention, said kit comprising one or more peptides selected from the list comprising SEQ ID No: 1, SEQ ID No: 4, or SEQ ID No: 8, or a fragment comprising at least 4, in particular at least 5, even more in particular at least 6, consecutive amino acids derived therefrom; and reagents for detecting antibody binding to said one or more peptides or fragments therefrom.

In still another aspect, a diagnostic kit is provided for performing the in vitro method according to the present invention, said kit comprising peptides selected from the list comprising SEQ ID No: 1, SEQ ID No: 4, and SEQ ID No: 8, or a fragment comprising at least 4, in particular at least 5, even more in particular at least 6, consecutive amino acids derived therefrom; and reagents for detecting antibody binding to said one or more peptides or fragments therefrom.

In an even further aspect, a diagnostic kit is provided for performing the in vitro method according to the present invention, said kit comprising peptides selected from the list comprising SEQ ID No: 1, SEQ ID No: 4, and SEQ ID No: 8, or a fragment comprising at least 4, in particular at least 5, even more in particular at least 6, consecutive amino acids derived therefrom; said kit further comprising one or more peptides selected from the list comprising SEQ ID No: 2, SEQ ID No: 3, SEQ ID No: 5, SEQ ID No: 6, SEQ ID No: 7, or SEQ ID No: 9, or a fragment comprising at least 4, in particular at least 5, even more in particular at least 6, consecutive amino acids derived therefrom; and reagents for detecting antibody binding to said one or more peptides or fragments therefrom.

In a further embodiment, said diagnostic kits according to the different aspects of the invention are kits for use in ELISA, RIA, multiplex immunoassay, immunoblot, immunofluorescence assay, western blot, line assay, dot blot, or immuno microfluidics assays.

In a final aspect, the present invention provides a method for treatment of a subject with spondyloarthritis. In said method, the subject is first diagnosed with spondyloarthritis using any one of the in vitro methods, isolated polypeptides or compositions of the present invention, followed by selection of the therapy and treatment of the subject with the therapy against spondyloarthritis.

BRIEF DESCRIPTION OF THE DRAWINGS

With specific reference now to the figures, it is stressed that the particulars shown are by way of example and for purposes of illustrative discussion of the different embodiments of the present invention only. They are presented in the cause of providing what is believed to be the most useful and readily description of the principles and conceptual aspects of the invention. In this regard, no attempt is made to show structural details of the invention in more detail than is necessary for a fundamental understanding of the invention. The description taken with the drawings making apparent to those skilled in the art how the several forms of the invention may be embodied in practice.

FIG. 3B indicates the change in BASDAI score from baseline through the 12-month follow-up time point for patients positive for antibodies UH-axSpA-IgG.8. BASDAI, Bath Ankylosing Spondylitis Disease Activity Index. The cut-off for antibody positivity (1.3) is indicated by a dashed line.

DETAILED DESCRIPTION OF THE INVENTION

Figure 1A:
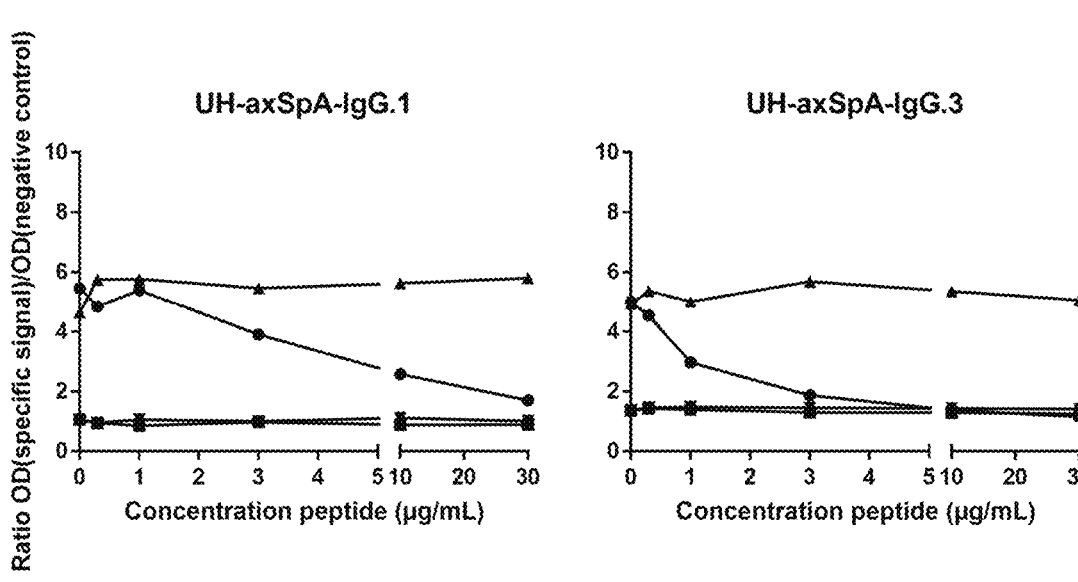
FIGS. 1A-1B Competition between synthetic peptide and peptide displayed on the phage surface. In a phage ELISA, an antibody-positive (P) and antibody-negative (N) plasma sample were pre-incubated in solution with increasing amounts of synthetic peptide, corresponding to the respective cDNA product displayed on the surface of each phage clone. As a negative control, both samples were also pre-incubated with increasing amounts of non-relevant peptide (control peptide). Within antibody-positive plasma samples (P), effective competition was detected for all six synthetic peptides tested (specific peptide), whereas no competition was seen after pre-incubation with control peptide and for antibody-negative plasma samples (N).
Figure 1A:
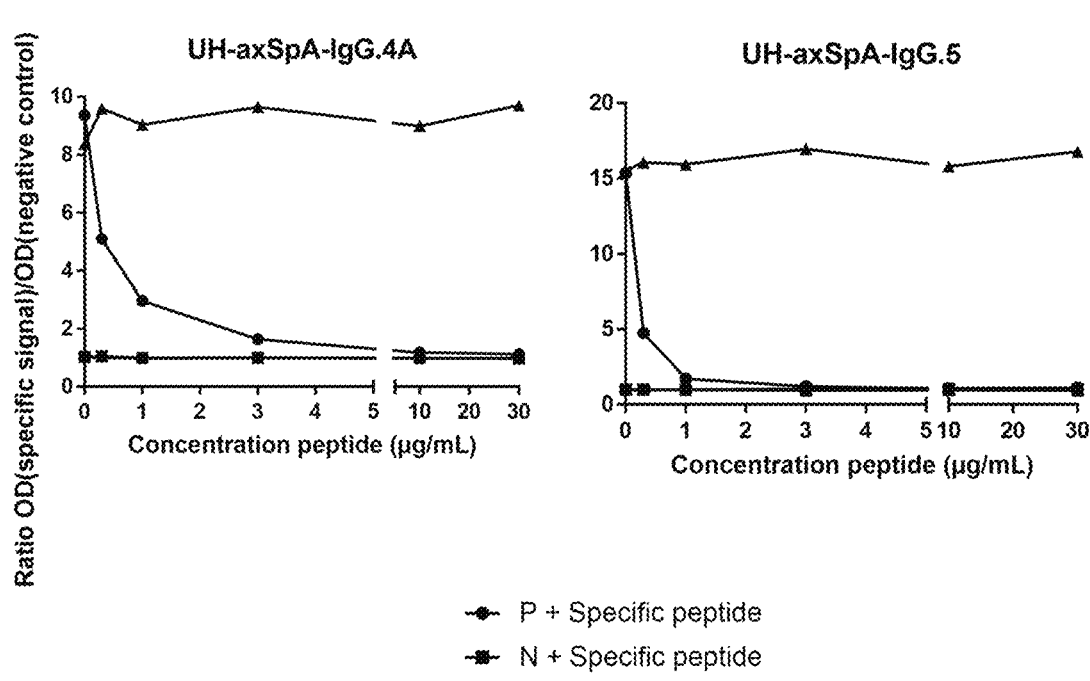

Recent evidence implicates antibody responses as possible novel players in spondyloarthritis. To date, only a limited number of antibody targets in spondyloarthritis and spondyloarthritis-associated diseases have been uncovered, and the discovery of novel targets with pathologic and clinical relevance still represents a major challenge.

In the current study, the aim was to perform an unbiased screening to identify novel (auto)antibodies in early axSpA patients that might provide a novel tool for early axSpA diagnosis. To this end, we applied the antibody profiling technique serological antigen selection (SAS). In this approach, a cDNA phage display library constructed from axSpA hip synovial tissue was screened for reactivity with immunoglobulin G (IgG) antibodies in plasma of early axSpA patients.

In this study, we report the identification of autoantibodies to 9 novel Hassett University (UH)-axSpA peptides, including a novel axSpA autoantigen DUX4. The diagnostic value of autoantibodies to these novel UH-axSpA peptides was validated in axSpA patients and controls from two independent cohorts.

As already detailed herein before, in a first aspect, the present invention provides an in vitro method for diagnosing of spondyloarthritis, or for determining the risk of development of spondyloarthritis, or for evaluating the prognosis and/or disease severity of spondyloarthritis, for selecting a patient with spondyloarthritis for a specific treatment in a subject. Said method comprises:

a) providing a biological sample from the subject, and
b) determining autoantibody levels against one or more peptides selected from the list comprising SEQ ID NO: 1, SEQ ID NO: 2, SEQ ID NO: 3, SEQ ID No: 4, SEQ ID NO: 5, SEQ ID NO: 6, SEQ ID No: 7; SEQ ID NO: 8, or SEQ ID No: 9, or a fragment comprising at least 4 consecutive amino acids derived therefrom,
wherein the presence or an increase in autoantibody levels against said one or more peptides or fragments thereof in said biological sample compare to a reference sample is indicative for the diagnosis of spondyloarthritis, the risk of development of spondyloarthritis, for the prognosis and/or disease severity of spondyloarthritis or for selecting a patient with spondyloarthritis for a specific treatment of spondyloarthritis in the subject.

In a preferred aspect, autoantibody levels against the polypeptide comprising a sequence of SEQ ID No: 8, or a fragment comprising at least 4, preferably at least 6 consecutive amino acids derived therefrom are determined. In another preferred aspect, said autoantibody levels are combined with autoantibody levels against the polypeptide comprising a sequence of SEQ ID No 1 and/or 4, or a fragment comprising at least 4, preferably at least 6 consecutive amino acids derived therefrom.

In the context of the present invention, the sample may be any type of sample suitable for the determination of antibody levels against said one or more peptides of the invention, and is in particular blood, tissue or a body fluid, preferably selected from the list comprising hair, skin, nails, saliva, synovial liquid, blood serum, blood plasma, urine, tears, bone marrow fluid, cerebrospinal fluid, lymphatic fluid, amniotic fluid, nipple aspiration fluid, and the like; more preferably selected from blood serum or blood plasma.

The method of the present invention is in particular suitable for diagnosing the presence or for diagnosing the risk of development or for the therapy control of spondyloarthritis. The term "diagnosing" or "diagnosis" is meant to include "predicting" or "detecting" the presence of spondyloarthritis. Spondyloarthritis includes axial spondyloarthritis and peripheral spondyloarthritis; preferably selected from ankylosing spondylitis, non-radiographic axial spondyloarthritis, undifferentiated spondyloarthritis, juvenile spondyloarthritis, psoriasisarthritis.

Any suitable means for detecting antibody levels against one or more peptides of the present invention may be used. Methods for detecting antibody/antigen or immune complexes are well known in the art. The present invention may be modified by one skilled in the art to accommodate the various detection methods known in the art. The particular detection method chosen by one skilled in the art depends on several factors, including the amount of biological sample available, the type of biological sample, the stability of the biological sample, the stability of the antigen (i.e. peptide), and the affinity between the antibody and the antigen (i.e. peptide). For example, the method of the current invention may include the use of an immunoassay, such as, enzyme-linked immunosorbent assays (ELISAs), immunofluorescent techniques, radioimmunological assays (RIA) and immunoblotting and/or line blot. For example, in ELISA-based assays, antigens (i.e. peptides) are bound to a support, and the biological sample is combined therewith. Subsequently antibodies in the sample are allowed to bind to the antigens/peptides bound on the support, thereby forming immune complexes. After the immune complexes have formed, excess biological sample may be removed and the array may be washed to remove nonspecifically bound antibodies. The immune complexes may then be reacted with an appropriate enzyme-labeled anti-immunoglobulin. Then anti-immuno-globulin is allowed to react with the antibodies in the immune complexes. After an optional further wash, the enzyme substrate may be added. The enzyme linked to the anti-immunoglobulin catalyzes a reaction that converts the substrate into a product, which can then be detected and used to quantify the amount of antibody in the sample.

The peptides of the present invention are selected as such that no or only a marginal antibody reactivity is found in a reference sample in contrast to a significantly higher antibody reactivity in patients having spondyloarthritis. A reference sample is preferably a sample from a healthy individual not suffering from spondyloarthritis, or from an individual suffering from lower back pain without spondyloarthritis; in particular from non-inflammatory lower back pain without spondyloarthritis. On the other hand, a predetermined threshold based on healthy individuals may be set to compare samples from patients suspected of having spondyloarthritis. In a particular embodiment, antibody reactivity is determined by calculating the ratio of the optical density (OD) of the specific signal to OD of the background signal. For each peptide target, a cut-off for seropositivity was calculated as the mean of this ratio (OD (specific)/OD (background)) in the HC population plus 3*SD (after exclusion of outliers using the same formula). A sample is considered positive when its ratio (OD (specific)/OD (background)) is higher than this cut-off. In particular the higher the general reactivity (OD (specific)/OD (background)) for the peptides of the present invention, in a particular patient, the more likely it is that a positive diagnosis of spondyloarthritis is made.

While the methods of the present invention are highly useful in the diagnosis of spondyloarthritis, they are also very suitable for use in the diagnosis of the risk of development of spondyloarthritis or for therapy control of spondyloarthritis.

In some instances, antibodies against one or more of the peptides of the present invention are absent in healthy individuals, hence, in that instance, the mere detection or presence of an antibody response against said peptides or fragments thereof is already suitable for determining the diagnosis, prognosis or therapy control of spondyloarthritis in said patient.

In some other instances, the methods according to the different embodiments of the present invention can be combined with any other method available for the diagnosis of spondyloarthritis. Said other methods can be selected from physical examination, imaging technology and/or laboratory tests for human leukocyte antigen (HLA)-B27 and C-reactive protein (CRP).

Furthermore, although the method of the present invention is preferably performed with the (non-naturally) occurring peptides of the present invention, it can also be performed using their naturally occurring counterparts, i.e. proteins having regions that share homology with such peptides. In that respect, the peptides of the present invention were found to have homology with human proteins such as indicated in the table below:

| Peptide | Sequence[a] | Homology on protein level |
|---|---|---|
| SEQ ID No: 1 | (IP)GPAEHLQHQ* | 8/10 (80%) Eukaryotic translation initiation factor 4E type 2, EIF4E2 (O60573)<br>6/6 (100%) Adenylate cyclase type 8, ADCY8 (P40145)<br>8/13 (62%) Cyclic AMP-responsive element-binding protein 3-like protein, CREB3L4 (Q8TEY5) |
| SEQ ID No: 2 | (WA)PTSKTKDR* | 7/7 (100%) 1-phosphatidylinosital 4,5-biphosphate phosphodiesterase gamma-2, PLCG2 (P16885)<br>7/10 (70%) WD repeat-containing and planar cell polarity effector protein fritz homolog, WDPCP (O95876)<br>6/6 (100%) G patch domain-containing protein 1, GPATCH1 (Q9BRR8) |
| SEQ ID No: 3 | (WG)QAELMNKNGVGQKILHPL GLPNHLHRSFCPWLGLDFIRSFFWGR* | 7/9 (78%) D-amino acid oxidase activator, DAOA (P59103)<br>10/14 (71%) Autism susceptibility gene 2 protein, AUTS2 (Q8WXX7)<br>7/10 (70%) Leucine-rich repeat and IQ domain-containing protein 3, LRRIQ3 (A6PVS8) |
| SEQ ID No: 4 | (IP)ELLLWKIQP* | 6/7 (86%) G-protein coupled receptor 37-like 1 precursor, GPR37L1 (O60883)<br>6/9 (67%) 2-methoxy-6-polyprenyl-1,4-benzoquinol methylase, COQ5 |

-continued

| Peptide | Sequence$^a$ | Homology on protein level |
|---|---|---|
| | | (Q5HYK3)<br>6/7 (86%) Rap guanine<br>nucleotide exchange factor<br>1, RAPGEF1 (Q13905) |
| SEQ ID<br>No: 5 | (IP)ISTF* | 5/5 (100%) Mucin-16,<br>MUC16 (Q8WXI7)<br>5/6 (83%) Activating<br>transcription factor<br>7-interacting protein 1, ATF7IP<br>(Q6VMQ6)<br>5/5 (100%) F-box only<br>protein 47, FBXO47<br>(Q5MNV8) |
| SEQ ID<br>No: 6 | (IR)QRCSPPQLQHLGPEQC* | 9/13 (69%) Oxysterols<br>receptor LXR-alpha, NR1H3<br>(Q13133)<br>9/20 (45%) Transforming<br>acidic coiled-coil-containing<br>protein 2, TACC2 (O95359)<br>7/10 (70%) Histone-lysine<br>N-methyltransferase 2D,<br>KMT2D (O14686) |
| SEQ ID<br>No: 7 | (WA)ESYFPHQ* | 6/6 (100%) Intraflagellar<br>transport protein 56, TTC26<br>(A0AVF1)<br>8/15 (53%) Integrator<br>complex subunit 10, INTS10<br>(Q9NVR2)<br>5/5 (100%) TRAF3-<br>interacting JNK-activating<br>modulator, TRAF3IP3<br>(Q9Y228) |
| SEQ ID<br>No: 8 | (IP)PGELEALEGATSLEAPLSEEEYRALLEELQDA<br>RLGRGRLRAGRWPLFRREHL<br>AGYVGSCLPHATSTGLTSLGF<br>LPSRSRPGERLHTAETPHSGELPFFP<br>GHPGASRLGQRPDALHL<br>PLPCGGFRGHGLARWSC<br>PGFQFARCPGDL GSPDPAPPRTPLGSGWCKH<br>TLALCPHLSGPRLSHSARARQAVALQVPVL<br>PAFPQVQRPPRSLRVGESPFQRSRGGVGKIP<br>TCRGRLGHPRCRCGLAGLEGTAAAN* | 26/29 (90%) Double<br>homeobox protein 4-like,<br>DUX4 (Q9UBX2)<br>21/47 (45%) 26S<br>proteasome non-ATPase<br>regulatory subunit 5, PSMD5<br>(Q16401)<br>21/45 (47%)<br>Phosphatidylinositol<br>4,5-bisphosphate<br>5-phosphatase A, INPP5J<br>(Q15735) |
| SEQ ID<br>No: 9 | (LG)ARTKAAVAQ* | 7/9 (78%) FRAS1-related<br>extracellular matrix protein<br>1, FREM1 (Q5H8C1)<br>6/8 (75%) Transmembrane<br>and coiled-coil domains<br>protein 1, TMCC1 (O94876)<br>6/7 (86%) RIMS-binding<br>protein 2, RHVIBP2 (O15034) |

$^a$Peptide sequence of the translated cDNA insert, with the first aa between parenthesis representing the last full aa of the adaptor sequence and the second aa between parenthesis representing the aa formed by the fusion between the adaptor and the cDNA insert.
Q Amber stop codon, which is translated into glutamine by the bacterial strain
*stop codon Hence, in a further aspect, the present invention provides an in vitro method for diagnosing the presence or for diagnosing the risk of development, or for the therapy control of spondyloarthritis in a subject, said method comprising:

a) providing a biological sample from the subject, and b) determining autoantibody levels against one or more peptides selected from the list comprising SEQ ID NO: 1, SEQ ID No: 4 or SEQ ID NO: 8, or a fragment comprising at least 4; in particular at least 6, consecutive amino acids derived therefrom;

wherein an increase in autoantibody levels against said one or more peptides or fragments thereof in said biological sample compared to a reference sample is indicative for the presence or the risk of development, or for the therapy control of spondyloarthritis.

In still another aspect, the present invention provides an in vitro method for diagnosing of spondyloarthritis, or for determining the risk of development of spondyloarthritis, or for evaluating the prognosis and/or disease severity of spondyloarthritis, for selecting a patient with spondyloarthritis for a specific treatment in a subject, said method comprising:

a) providing a biological sample from the subject, and b) determining autoantibody levels against peptides selected from the list comprising SEQ ID No: 1, SEQ ID No: 4, and SEQ ID No: 8, or a fragment comprising at least 4 consecutive amino acids derived therefrom;

wherein an increase in autoantibody levels against said peptides or fragments thereof in said biological sample compared to a reference sample is indicative for the diagnosis of spondyloarthritis, for the risk of development of spondyloarthritis, for the prognosis and/or disease severity of spondyloarthritis or for selecting a patient with spondyloarthritis for a specific treatment of spondyloarthritis in the subject.

In still another aspect, polypeptides are selected from the list comprising SEQ ID NO: 1, SEQ ID No: 4 and SEQ ID NO: 8, or a fragment comprising at least 4 consecutive amino acids derived therefrom; in particular at least 6 consecutive amino acids derived therefrom.

In all aspects of the invention, any combination of two or more polypeptides selected from the list comprising SEQ ID No 1-9, can suitably be used within the context of the present invention; preferably polypeptides are selected from the list comprising SEQ ID Nos 1, 4 and 8. The peptides of the present invention may be provided as such, however, also fragments comprising at least 4, at least 5, in particular at least 6, consecutive amino acids derived therefrom are suitable for use in the method of the current invention. Hence, at any mentioning of a "full-length" peptide, it may alternatively be replaced by a fragment, comprising at least 4; at least 5, or at least 6 consecutive amino acids derived therefrom.

The present invention also provides isolated polypeptides comprising a sequence represented by any of SEQ ID Nos: 1-9, or a fragment comprising at least 4; preferably at least 6, consecutive amino acids derived from SEQ ID No: 1-9. In another aspect, the present invention provides isolated polypeptides consisting essentially of a sequence represented by SEQ ID Nos: 1-9, or a fragment comprising at least 4, preferably at least 6, consecutive amino acids derived from SEQ ID Nos: 1-9. Also compositions comprising the isolated polypeptides or a combination of isolated polypeptides are provided. The composition can also comprise at least two different polypeptides wherein said polypeptides are fragments comprising at least 4, at least 5, or at least 6 consecutive amino acids derived from SEQ ID No: 1, 2, 3, 4, 5, 6, 7, 8 or 9. It is envisaged that 4 and preferably 6 consecutive amino acids derived from SEQ ID No: 1-9 are sufficient to be recognized as antigens by the autoantibodies present in for example serum, plasma or synovial liquid or synovial fluid (SF).

In a particular embodiment, the composition thus comprises 3 different polypeptides comprising a sequence represented by SEQ ID NO: 1, 4, and 8, or 3 different fragments comprising at least 4, preferably at least 6 consecutive amino acids derived from SEQ ID NO: 1, 4 and 8.

In another embodiment, the invention also provides the use of a composition of the invention for detecting the presence of specific antibodies to at least one polypeptide present in said composition wherein said antibodies are present in a body fluid of a mammal.

In another particular embodiment, the invention provides the use of a composition of the invention for detecting the presence of specific autoantibodies to at least one polypeptide present in said composition wherein said autoantibodies are present in a body fluid of a mammal. In particular embodiments, said use of a composition is an "in vitro" use of a composition. The latter implies a diagnostic method with no direct interaction with the patient.

In yet another embodiment, the invention further provides an antibody that specifically binds to a polypeptide as described herein above. Methods for generating antibodies are well known in the art. In preferred embodiment, the antibodies are monoclonal antibodies. For the purpose of generation of antibodies, the polypeptides forming part of the compositions of the invention may be synthesized chemically or may be in a recombinant way. They may also be coupled to a soluble carrier after synthesis or after recombination production. If a carrier is used, the nature of such a carrier should be such that it has a molecular weight greater than 5000 and should not be recognized by antibodies. Such a carrier can be a protein. Proteins which are frequently used as carriers are keyhole limpet hemocyanin, bovine gamma globulin, bovine serum albumin, and poly-L-lysine. There are many well described techniques for coupling peptides to carriers. The linkage may occur at the N-terminus, C-terminus or at an internal site in the peptide. The polypeptide may also be derivatized for coupling. The polypeptides may also be synthesized directly on an oligo-lysine core in which both the alpha as well as the epsilon-amino groups of lysines are used as growth points for the polypeptides. The number of lysines comprising the core is preferably 3 or 7. Additionally, a cysteine may be included near or at the C-terminus of the complex to facilitate the formation of homo- or heterodimers.

In general terms, the invention relates to a process for detecting antibodies related to spondyloarthritis in a biological sample of a subject, preferably a human, liable to contain them. This process comprises contacting the biological sample with a composition according to the invention under conditions enabling an immunological reaction between said composition and the antibodies which are possibly present in the biological sample and the detection of the antigen/antibody complex which may be formed. The detection can be carried out according to any classical process. By way of examples immunoenzymatic process according to the ELISA technique or immunofluorescent or radioimmunological (RIA) or the equivalent ones (e.g. LINE blot or LINE assay) can be used. Thus the invention relates to polypeptides according to the invention labelled by an appropriate label of the enzymatic, fluorescent, biotin, radioactive type. Such a method for detecting antibodies related to spondyloarthritis comprises for instance the following steps: deposit of determined amounts of a polypeptidic composition according to the invention on a support (e.g. into wells of a titration microplate), introduction on said support (e.g. into wells) of increasing dilutions of the body fluid (e.g. blood plasma or serum) to be diagnosed, incubation of the support (e.g. microplate), repeated rinsing of the support (e.g. microplate), introduction on the support labelled antibodies which are specific for immunoglobulins present in the body fluid, the labelling of these antibodies being based on the activity of an enzyme which is selected from among the ones which are able to hydrolyze a substrate by modifying the absorption of the radiation of this latter at least at a given wave length, detection by comparing a control standard of the amount of hydrolyzed substrate.

In yet another aspect, the invention also relates to a process for detecting and identifying antigen of spondyloarthritis in a body fluid liable to contain them, this process comprising contacting the biological sample with an appropriate antibody of the invention (i.e. antibodies with a specificity for a polypeptide of the composition) under conditions enabling an immunological reaction between said antibody and the antigens of spondyloarthritis which are possibly present in the biological sample and the detection of the antigen/antibody complex which may be formed.

Thus antibodies, in particular auto-antibodies, which recognize the polypeptides of the invention, can be detected in a variety of ways. One method of detection is further described in the examples and uses enzyme-linked immunosorbent assay (ELISA) of the polypeptides of the invention displayed by phages (e.g. phage-ELISA technology). The latter technology is fully described in (18), wherein paragraph 2.6 on page 225 is herein specifically incorporated. In other ways, the detection in ELISA uses a polypeptide or mixture of polypeptides bound to a solid support. In some cases, this will be a microtiter plate but may in principle be any sort of insoluble solid phase (e.g. glass, nitrocellulose). In one embodiment a suitable dilution or dilutions of for example blood or serum to be tested is brought into contact with the solid phase to which the polypeptide is bound. In another embodiment "a solution hybridization" is carried out in which high affinity interactions occur (e.g. biotinylated polypeptides of the composition are pre-incubated with serum). The incubation is carried out for a time necessary to allow the binding reaction to occur. Subsequently, unbound components are removed by washing the solid phase. The detection of immune complexes (i.e. autoantibodies present in for example human serum binding to at least one polypeptide of the invention) is achieved using antibodies which specifically bind to human immunoglobulins, and which have been labelled with an enzyme, preferably but not limited to either horseradish peroxidase, alkaline phosphatase, or beta-galactosidase, which is capable of converting a colourless or nearly colourless substrate or co-substrate into a highly colored product or a product capable of forming a colored complex with a chromogen. Alternatively, a detection system may employ an enzyme which, in the presence of the proper substrate(s), emits light. The amount of product formed is detected either visually, spectrophotometrically, electrochemically, fluorescently or luminometrically, and is compared to a similarly treated control. The detection system may also employ radioactively labelled antibodies, in which cases the amount of immune complex is quantified by scintillation counting or gamma counting. Other detection systems which may be used include those based on the use of protein A derived from *Staphylococcus aureus* Cowan strain I, protein G from group C *Staphylococcus* sp. (strain 26RP66), or systems which make use of the high affinity biotin-avidin or streptavidin binding reaction.

The polypeptides of the invention may be either labelled or unlabelled. Labels which may be employed may be of any type, such as enzymatic, chemical, fluorescent, luminescent, or radioactive. In addition, the polypeptides may be modified for binding to surfaces or solid phases, such as, for example microtiter plates, nylon membranes, glass or plastic beads, and chromatographic supports such as cellulose, silica, or agarose. The methods by which polypeptides can be attached or bound to solid support or surface are well known to those skilled in the art.

The polypeptides of the invention can be prepared according to the classical techniques in the field of peptide synthesis. The synthesis can be carried out in homogeneous solution or in solid phase. For instance, the synthesis technique in homogeneous solution which can be used is the one described by Houbenweyl in the book titled "Methode der organische chemie" (Method of organic chemistry) edited by E. Wunsch, vol. 15-I et II. THIEME, Stuttgart 1974. The polypeptides of the invention can also be prepared in solid phase according the the method described by Atherton & Shepard in their book titled "Solid phase peptide synthesis" (Ed. IRL Press, Oxford, NY, Tokyo, 1989). Synthesis protocols in the art generally employ the use of t-butyloxycarbonyl- or 9-fluorenylmethoxy-carbonyl-protected activated amino acids. The procedures for carrying out the syntheses, the types of side-chain protection, and the cleavage methods are amply described in, for example, Stewart and Young, Solid Phase Peptide Synthesis, $2^{nd}$ Edition, Pierce Chemical Company, 1984; and Atherton and Sheppard, Solid Phase Peptide Synthesis, IRL Press 1989.

In yet another embodiment antibodies raised to polypeptides of the invention (or carrier-bound polypeptides) can also be used in conjunction with labelled or unlabelled polypeptides of the invention for the detection of (auto) antibodies present in serum by competition assay. For example, antibodies raised to polypeptides are attached to a solid support which may be, for example, a plastic bead or a plastic tube. The polypeptide is then mixed with suitable dilutions of the fluid (e.g. serum) to be tested and this mixture is subsequently brought into contact with the antibody bound to the solid support. After a suitable incubation period, the solid support is washed and the amount of labelled or unlabelled polypeptide is quantified. A reduction in the amount of label bound to the solid support is indicative of the presence of (auto)antibodies in the original sample, such as blood plasma or serum. By the same token, the polypeptide may also be bound to the solid support. Labelled antibody may then be allowed to compete with (auto)antibody present in the sample (e.g. serum) under conditions in which the amount of polypeptide is limiting. As in the previous example, a reduction of the measured signal is indicative of the presence of (auto)antibodies in the sample tested.

In another embodiment, a competition ELISA can be used in which samples (e.g. plasma samples) are pre-incubated with increasing concentrations of one or more synthetic peptides corresponding to the sequences defined by SEQ ID No: 1-9, before use in a phage ELISA.

In a particular embodiment a test for giving evidence of the fact that one or more polypeptides present in a composition of the invention are recognized by antibodies present in for example blood or serum (for example auto-antibodies present in serum of spondyloarthritis patients) is an immunoblotting (or Western blotting) analysis. In the latter case polypeptides can be chemically synthesized or polypeptides (or the protein) can be produced via recombinant techniques. In short, after sodium dodecyl sulfate-polyacrylamide gel electrophoresis, polypeptides of the invention are blotted onto nitrocellulose membranes (e.g. Hybond C. (Amersham)) as described by Towbin H. et al., 1979, "Electrophoretic transfer of proteins from polyacrylamide gels to nitrocellulose sheets: procedure and some applications", Proc. Natl. Acad. Sci. USA 76:4350-4354.

It goes without saying that the free reactive functions which are present in some of the amino acids, which are part of the constitution of the polypeptides of the invention, particularly the free carboxyl groups which are carried by the groups Glu and Asp or by the C-terminal amino acid on the one hand and/or the free NH2 groups carried by the N-terminal amino acid of by amino acids inside the peptidic chain, for instance Lys, on the other hand, can be modified in so far as this modification does not alter the above mentioned properties of the polypeptide. The polypeptides which are thus modified are naturally part of the invention. The above mentioned carboxyl groups can be acylated or esterified. Other modifications are also part of the invention. Particularly, the amine or carboxyl functions or both of terminal amino acids can be themselves involved in the bond with other amino acids. For instance, the N-terminal amino acid can be linked to the C-terminal amino acid of another peptide comprising from 1 to several amino acids. Further- more, any peptidic sequences resulting from the modifica- tion by substitution and/or by addition and/or by deletion of one or several amino acids of the polypeptides according to the invention are part of the invention in so far as this modification does not alter the above mentioned properties of said polypeptides. The polypeptides according to the invention can be glycosylated or not, particularly in some of their glycosylation sites of the type Asn-X-Ser or Asn-X- Thr, X representing any amino acid.

Variations of these polypeptides are also possible depend- ing on its intended use. For example, if the polypeptide is to be used to raise antisera, the polypeptide may be synthesized with an extra cysteine residue added. This extra cysteine residue is preferably added to the amino terminus and facilitates the coupling of the polypeptide to a carrier protein which is necessary to render the small polypeptide immu- nogenic. If the polypeptide is to be labeled for use in radioimmune assays, it may be advantageous to synthesize the protein with a tyrosine attached to either the amino or carboxyl terminus to facilitate iodination. This polypeptide possesses therefore the primary sequence of the polypeptide above-mentioned but with additional amino acids which do not appear in the primary sequence of the protein and whose sole function is to confer the desired chemical properties to the polypeptide.

The present invention also provides a diagnostic kit for performing one of the in vitro methods according to the present invention, said kit comprising one or more polypep- tides of the invention or a composition according to an embodiment of the invention; and reagents for detecting antibody binding to said one or more peptides or fragments therefrom. Said reagents are for example reagents for mak- ing a medium appropriate for the immunological reaction to occur, reagents enabling the antigen/antibody complex which has been produced by the immunological reaction, said reagents possibly having a label, or being liable to be recognizable by a labelled reagent, more particularly in the case where the abovementioned polypeptide is not labelled.

In a further embodiment, one or more polypeptides, or the immune reactive peptides thereof, for use in the diagnosis, risk assessment or therapy control of spondyloarthritis, are provided, wherein said one or more polypeptides comprise an epitope having a sequence selected from any one of SEQ ID No: 1 to 9, or a fragment comprising at least 4, in particular at least 5, even more in particular at least 6, consecutive amino acids derived therefrom. In still a further embodiment, said one or more polypeptides or the immune reactive peptides thereof comprise an epitope having a sequence selected from any one of SEQ ID No: 1, SEQ ID No: 4, or SEQ ID No: 8, or a fragment comprising at least 4, in particular at least 5, even more in particular at least 6, consecutive amino acids derived therefrom. In another fur- ther embodiment, said one or more polypeptides, or the immune reactive peptides thereof, preferably being in form of a pharmaceutical composition, are for use in the prophy- laxis and/or treatment of spondyloarthritis, wherein said one or more polypeptides comprise an epitope having a sequence selected from any one of SEQ ID No: 1 to 9, or a fragment comprising at least 4, in particular at least 5, even more in particular at least 6 consecutive amino acids derived there- from. In particular, said one or more polypeptides or the immune reactive peptides thereof comprise an epitope hav- ing a sequence selected from any one of SEQ ID No: 1, SEQ ID No: 4, or SEQ ID No: 8, or a fragment comprising at least 4, in particular at least 5, even more in particular at least 6, consecutive amino acids derived therefrom.

In a final aspect, a method for treatment of a subject with spondyloarthritis is provided. In said method, the subject is first diagnosed with spondyloarthritis using any one of the in vitro methods, isolated polypeptides, compositions or diag- nostic kits of the present invention, followed by selection of the appropriate therapy and treatment of the subject with said therapy against spondyloarthritis. For example, the method of treatment comprises the in vitro method for diagnosing the presence of spondyloarthritis in a subject, said method being any method as described herein above, followed by treatment of the subject diagnosed with spon- dyloarthritis with a therapy selected from nonsteroidal anti- inflammatory drugs (NSAIDs), conventional disease-modi- fying anti-rheumatic drugs (cDMARDs) and biological DMARDs such as tumor necrosis factor-alpha (TNF-alpha) inhibitors.

Other characteristics and advantages of the invention will appear in the following examples and the figures illustrating the invention.

EXAMPLES

Materials and Methods

Patients and Controls

Synovial tissues from the hip of 3 axSpA patients were collected during primary hip arthroplasty at Hospital East- Limburg. Tissues were snap frozen in liquid nitrogen and stored at −80° C. in collaboration with the University Biobank Limburg (UBiLim).

Plasma of axSpA patients was collected at a rheumatology center in Genk (UH cohort) (n=86) and at University Hos- pitals Leuven ((Bio)SPAR cohort) (n=174) (10, 11). All axSpA patients from the UH cohort (n=86) and 79 patients from the (Bio)SPAR cohort, which had a maximum diag- nosis of 5 years, were considered early patients.

As controls, plasma from patients with chronic low back pain (LBP) (n=75), rheumatoid arthritis (RA) (n=60) and from healthy controls (HC) (n=104) was collected in Hasselt and Genk.

All axSpA patients were diagnosed by their treating rheumatologist and classified according to the Assessment of SpondyloArthritis international Society (ASAS) classifica- tion criteria (2). Patients with RA fulfilled the 1987 Ameri- can College of Rheumatology criteria for RA (12), and chronic LBP was diagnosed according to the European guidelines for the management of chronic non-specific LBP (13).

This study was approved by the local Ethical Committees of Jessa Hospital, Hasselt University and Hospital East Limburg, and by the Ethical Committee for Clinical Research at University Hospitals Leuven. All patients and controls provided informed consent. All human biological material used in this publication was kindly provided by the University Biobank Limburg (UBiLim) and the Biobank of University Hospitals Leuven.

Clinical Parameters and Groups of Interest

Novel autoantibodies in axSpA patients were identified by the SAS procedure, using pooled plasma of axSpA patients and HC. The early axSpA SAS pool consisted of 10 axSpA patients from the UH cohort which did not receive biologics therapy, with a mean age of 40.6±11.8 years, a mean disease duration of 1.4±0.5 years, 5 (50%) were male and 8 (80%) were HLA-B27 positive. The HC SAS pool consisted of 10 HC plasma samples, which were age- and gender-matched to the axSpA pool (mean age of 40.6±12.3 years and 5 (50%) were male).

Antibody reactivity towards individual identified peptides from the SAS procedure was determined in additional pools of early axSpA patients (n=60) and HC (n=30), 10 individuals per pool. These 60 axSpA patients had a mean age of 44.1±13.3 years, a mean disease duration of 3.0±1.6 years, 36 (60%) were male and 38 (63.2%) were HLA-B27 positive. The 30 HC had a mean age of 46.7±18.5 years and 4 (40%) were male.

Antibody reactivity against selected peptides was further validated in individual plasma samples of 76 early axSpA patients, 75 persons with LBP, 60 RA patients and 94 HC from the UH cohort and in serum samples of 174 axSpA patients, including 79 early axSpA patients from the (Bio) SPAR cohort.

Clinical characteristics of all included axSpA patients from both the UH and (Bio)SPAR cohort are summarized in Table 1. In brief, axSpA patients from the UH cohort and (Bio)SPAR cohort had a mean age of 43.2±12.7 years and 41.9±12.8 years, respectively. Mean age of the early axSpA patients from the (Bio)SPAR cohort was 36.4±11.7 years and was significantly lower (p=0.0007). In the UH cohort, 57% of axSpA patients were male as compared to 66% of all axSpA patients (p=0.1571) and 61% of early axSpA patients (p=0.6273) from the (Bio)SPAR cohort. Fifty-nine % of axSpA patients in the UH cohort was HLA-B27 positive, compared to 86% of all axSpA patients (p=<0.0001) and 83% of early axSpA patients (p=0.0026) from the (Bio) SPAR cohort. The mean disease duration of axSpA patients from the UH cohort was 2.8±1.4 years, whereas all axSpA patients and early axSpA patients from the (Bio)SPAR cohort had a disease duration of respectively 10.4±10.9 years (p=<0.0001) and 1.4±1.7 years (p=<0.0001).

Healthy controls (n=94) had a mean age of 44.6±18.4 years and 52 (55%) were male. Persons with LBP (n=75) had a mean age of 45.5±9.2 years, 34 (45%) were male and had a mean duration of low back pain complaints of 10.7±9.3 years. RA patients (n=60) had a mean age of 51.6±11.5 years, a mean disease duration of 3.1±1.2 years, 30 (50%) were male and 57 (95%) received conventional disease modifying antirheumatic drugs (cDMARDs).

Construction of Human axSpA cDNA Phage Display Library

A human axSpA cDNA phage display library was constructed according to the procedure as described in (14). In brief, total RNA was extracted from hip synovial tissue of 3 axSpA patients and messenger RNA (mRNA) was converted into double-stranded cDNA, using the Maxima H-minus double-stranded cDNA synthesis kit (Thermo Fisher Scientific, Belgium). Patient-specific adaptors were ligated to the cDNA, which was then size-fractionated by agarose gel electrophoresis. Subsequently, cDNA molecules ranging from 200 to 10,000 basepairs were directionally cloned into the pSPVI-A/B/C phagemid vectors (15) and transformed in TG1 E.coli cells via electroporation. Phage particles from this resulting cDNA phage display library were produced by infecting TG1 E.coli cells with M13K07 helper phage and purifying via PEG/NaCl precipitation.

Identification of Novel Autoantibodies by Serological Antigen Selection (SAS)

SAS was used as screening procedure to identify the antigenic targets of novel autoantibodies in early axSpA patients. To this end, the cDNA phage display library was screened for IgG antibody reactivity present in the early axSpA SAS pool, using the previously described SAS procedure (16-19) with some minor modifications. To prevent the isolation of common antibodies present in HC and to enrich for axSpA specific antibodies, counterselection was performed with the HC SAS pool. Peptides displayed on the phage surface, were identified by sequencing the fusion of M13 gene pVI with the cDNA inserts (14). The custom-made DNAnalyzer program, based on an Anaconda Phyton multiprocessing module, allowed automation of the comparison of nucleotide and amino acid (aa) sequences to human sequences with the basic local alignment search tool (BLAST) of NCBI.

Detection of Autoantibodies to 9 Novel UH-axSpA-IgG Peptides

Antibody reactivity against peptides displayed on phage was measured by phage enzyme linked immunosorbent assays (phage ELISA) in pooled or individual plasma samples. Half area 96 well Microlon high binding microplates (Greiner, Belgium) were coated overnight at 4° C. with 3.5 μg/mL anti-M13 mouse monoclonal antibody (clone MM05T, Sino Biological, China) diluted in coating buffer (0.2 M sodium carbonate bicarbonate buffer, pH 9.6). Plates were washed using phosphate-buffered saline with Tween 20 (PBS-T;1.54 mM KH2PO4, 5.62 mM Na2HPO4, 130 mM NaCl, pH 7.4, 0.1% (v/v) Tween 20) and PBS and blocked for 2 h at 37° C. at 100 rpm with 5% (w/v) skimmed milk powder in PBS (MPBS). Subsequently, plates were washed three times with PBS-T and once with PBS. The plates were incubated with $7 \times 10^{11}$ colony forming units/mL of phage particles displaying peptides of interest (specific phage) or phage particles without peptide (empty phage) for 1 h at 37° C. and 30 min at room temperature (RT) at 100 rpm. Plates were washed and incubated with plasma diluted ¹⁄₁₀₀ in MPBS for 1 h at 37° C. and 30 min at RT at 100 rpm. Plates were washed and incubated with secondary antibody, cross-adsorbed goat anti-human IgG-Fc conjugated with horse radish peroxidase (Bethyl, United States) diluted ¹⁄₁₀,₀₀₀ in 5% MPBS, for 1 h at RT at 100 rpm.

Antibody reactivity against each peptide target is expressed by the ratio of the optical density (OD) signal of each phage-displayed peptide over the OD signal of the phage without peptide (OD(specific phage)/OD(empty phage)). For each peptide target, a cut-off for seropositivity was calculated as the mean of the antibody reactivity in the HC population plus 3*SD (after exclusion of outliers using the same formula).

Competition ELISA is a variant of the phage ELISA where plasma samples were first pre-incubated with synthetic peptide, corresponding to the respective peptide displayed on the phage surface. For each peptide target, a positive and a negative plasma sample were pre-incubated with increasing concentrations (0-30 μg/mL) of one of six synthetic peptides (>85% purity, GL Biochem, China), corresponding to the peptide sequence of UH-axSpA-IgG.1, UH-axSpA-IgG.3, UH-axSpA-IgG.4, UH-axSpA-IgG.5, UH-axSpA-IgG.6 and UH-axSpA-IgG.8, before use in phage ELISA. Synthetic peptide sequences are indicated in Table 2. Peptide sequence UH-axSpA-IgG.5 was extended at the N-terminus with the translated adaptor sequence (ENSRPRIPISTF; SEQ ID No: 10), and for UH-axSpA-IgG.8, only the part corresponding to the DUX4 C-terminus was used (IPPGELEALEGATSLEAPLSEEEYRALLEEL; SEQ ID No: 11). Increasing amounts of control peptide (WTKTPDGNFQLGGTEP; SEQ ID No: 12) were used as a control.

For each condition, the reactivity of the remaining antibody not bound by synthetic peptide is expressed as the ratio of the OD signal of the specific peptide to the OD signal of the control peptide (OD(specific peptide)/OD(control peptide)).

Within each phage ELISA experiment, samples were tested in duplicate and experiments were performed independently at least twice. Average values of experimental repeats had a coefficient of variation (% CV) lower than 20%.

UH-axSpA-IgG.8 Peptide ELISA

The synthetic peptide corresponding to the phage-displayed peptide UH-axSpA-IgG.8 was commercially obtained (>85% purity GL Biochem, Shanghai, China). Antibody reactivity against UH-axSpA-IgG.8 was measured by a peptide-based ELISA. Briefly, all samples were tested on both the specific peptide (UH-axSpA-IgG.8: IPPGEL-EALEGATSLEAPLSEEEYRALLEEL; SEQ ID No: 11) and the irrelevant control peptide (WTKTPDGNFQLGGTEP; SEQ ID No: 12). Synthetic peptides were coated overnight at room temperature (RT) at 2 µg/mL in phosphate-buffered saline (PBS; 1.54 mM KH2PO4, 5.62 mM Na2HPO4, 130 mM NaCl, pH 7.4) in ELISA plates (polystyrene half-area flat-bottom microplates, Greiner Bio-One, Wemmel, Belgium). After washing, plates were blocked with 100 µL/well of PBS containing 2% (w/v) skimmed milk powder (MPBS) for 2 hours (h) shaking at 37° C. Plates were washed during 5 minutes (min) for three consecutive times. Samples were diluted in 2% MPBS (1:100 for IgA and IgG and 1:50 for IgM detection) and were incubated at RT for 2 h (50 µL/well, shaking). After washing, antibody binding was detected using a polyclonal horseradish peroxidase conjugated rabbit anti-human IgG secondary antibody (1:2000) (Dako, Heverlee, Belgium), rabbit anti-human IgA secondary antibody (1:500) (Dako) and goat anti-human IgM secondary antibody (1:5000) (Sigma-Aldrich, Diegem, Belgium), respectively and diluted in MPBS. 50 µL/well was applied for 1 h shaking at RT. Following washing, staining was performed in the dark with 100 µL 3,3',5,5'-tetramethylbenzidine (TMB; Thermo Scientific). The reaction was stopped with 25 µL 2N $H_2SO_4$ and results were read at 450 nm (Microplate reader Infinite M1000 Pro, TECAN, Mannedorf, Switzerland). Washing steps were performed with PBS containing 0.05% (v/v) Tween-20 (VWR, Leuven, Belgium). Antibody reactivity against the peptide is expressed by the ratio of the optical density (OD) signal of the specific peptide over the OD signal of the control peptide (OD(specific peptide)/OD(control peptide)). A ratio of >1.3 was considered positive in the ELISA. The UH-axSpA-IgG.8 peptide-based ELISA was used to determine the presence of different antibody isotypes and to investigate the effect of therapy on antibody levels.

Immunohistochemical Analysis of DUX4 Expression in Synovial Tissue

Cryosections of synovial hip tissue of an axSpA patient were dried for 30 min at RT, fixated for 10 min in ice-cold acetone and dried for 30 min at RT. Synovial histology was revealed by haematoxylin and eosin (H&E) staining. For fluorescent stainings, cryosections were washed three times with PBS and blocked for 30 min at RT with 100% protein block (Dako). Subsequently, mouse monoclonal anti-human DUX4 antibody (clone P4H2, Thermo Fisher Scientific), was diluted ⅟100 in PBS with 0.5% Triton X-100 and added to the sections. After overnight incubation in a humidified chamber at 4° C., tissue sections were washed and incubated with goat polyclonal anti-mouse IgG secondary antibody conjugated with Alexa Fluor 555 (Life Technologies, Belgium) diluted ⅟600 in PBS with 0.5% Triton X-100. Cell nuclei were counterstained in 300 nM 4',6-diamidino-2-phenylindol (DAPI; Thermo Fisher Scientific) for 10 min at RT and mounted with fluorescence mounting medium (Dako). As a negative control, no primary anti-DUX4 antibody was added. Fluorescent images were taken with a Leica DM4000 B LED microscope and a Leica DFC 450c camera, whereas H&E images were taken with a Leica DM2000 LED and a Leica MC170 HD camera (Leica microsystems, Belgium).

Statistical Analysis

All statistical analyses were performed using SAS JMP Pro version 13.2 and a P value of <0.05 was considered statistically significant. Presence of antibodies to particular UH-axSpA-IgG peptides or panels of peptides was compared between axSpA patients and controls by applying Fisher's exact test. Continuous clinical characteristics between antibody-positive and antibody-negative axSpA patients were compared using Students t-tests, whereas categorical characteristics were compared by Fisher's exact tests.

The positive likelihood ratio (LR+) of antibodies against particular UH-axSpA-IgG peptides or panels of peptides were calculated based on their presence in axSpA patients and persons with LBP. Applying the method described by Rudwaleit et al (20), posttest probabilities could be calculated based on the assumption that the prevalence of axSpA among patients with LBP is 5% and the LR+.

Results

Screening for Novel Autoantibody Targets in Early axSpA Patients

We constructed a human axSpA cDNA phage display library from hip synovial tissue of 3 axSpA patients with a large diversity of $1.88 \times 10^6$ recombinant clones. Approximately 23% ($2.6 \times 10^6$) of the clones of this library expressed (fragments of) known human proteins, indicating that this library is of high quality and provides a good representation of the antigenic heterogeneity within axSpA synovial hip tissue. The remaining part of the library consists of out-of-frame cDNA fusions that generate random peptide sequences.

Using this axSpA cDNA phage display library to screen for antibody reactivity in the axSpA SAS pool using serological antigen selection (SAS), resulted in the identification of novel IgG antibodies against 105 different peptides displayed on the phage surface.

Testing antibody reactivity against each of these 105 individual peptides in plasma pools of 60 early axSpA patients and 30 age- and gender-matched HC, resulted in 9 peptides against which antibody reactivity was more frequently present in early axSpA patients than HC (data not shown). These 9 peptides were called UH-axSpA-IgG.1 till UH-axSpA-IgG.9 (University Hasselt-axSpA-IgG isotype.target number).

Identity of UH-axSpA-IgG Peptides Targeted by Novel axSpA Autoantibodies

Nucleotide and amino acid (aa) sequences of the 9 selected UH-axSpA-IgG peptides were compared to human sequences using the BLAST tool of NCBI and the custom DNAnalyzer program (Table 2). The peptide sequences expressed by UH-axSpA-IgG.1-7 and UH-axSpA-IgG.9 had a length between 6 and 46 aa and resulted from the out-of-frame translation or translation of non-coding sequences and therefore showed only partial homology to different human proteins.

The DNA sequence of UH-axSpA-IgG.8 corresponded with an in-frame fusion to the 3'-coding region and 3'-untranslated region (UTR) of the human Double homeobox protein 4 (DUX4) gene. However, our sequencing analysis of multiple synovial DUX4 transcripts showed that this gene was hypervariable in the region analysed. Sequencing of 34 cloned DUX4 transcripts revealed 24 different variants with 1 to 9 single nucleotide polymorphisms over the 89 nucleotide sequence corresponding to the UH-axSpA-IgG.8 clone (results not shown). Our isolated DUX4 variant showed 93% homology with the canonical DUX4 sequence (NM_001306068.2), resulting in the expression of a DUX4 C-terminal fragment with 26 to 29 aa homology (data not shown). In addition, as amber stop codons (UAG) are translated to glutamine in the bacterial strain used to produce the phage clones, this sequence was followed by 221 aa resulting from the translation of the 3'UTR sequence.

Presence of axSpA antibodies to 9 novel UH-axSpA-IgG peptides in two independent cohorts Antibody reactivity against the 9 UH-axSpA peptides was further validated in individual plasma samples of early axSpA patients and controls from the UH cohort. Antibodies against individual UH-axSpA-IgG peptides were present in 3% ($^2$/$_{76}$) to 13% ($^{10}$/$_{76}$) of early axSpA patients (Table 3). Antibodies against at least one of the 9 peptides were found in 54% ($^{41}$/$_{76}$) of early axSpA patients from the UH cohort, 26% ($^{24}$/$_{94}$) of HC (p=0.0002), 39% ($^{29}$/$_{75}$) of LBP (p=0.0731) and 38% ($^{23}$/$_{60}$) of RA patients (p=0.0845).

Presence of these antibodies was also confirmed in 174 axSpA patients from the independent (Bio)SPAR cohort, including 79 axSpA patients with an early disease course (Table 3). Within all axSpA patients from the (Bio)SPAR cohort, antibody reactivity against individual peptides was found in 2% ($^4$/$_{174}$) to 18% ($^{32}$/$_{174}$) of patients, while antibodies against at least one of the 9 UH-axSpA-IgG peptides were present in 43% ($^{74}$/$_{174}$) of these patients.

Furthermore, antibody reactivity against individual peptides was found in 1 ($^1$/$_{79}$) to 10% ($^8$/$_{79}$) of early axSpA patients from the (Bio)SPAR cohort while antibodies against at least one of the 9 peptides were demonstrated in 34% ($^{27}$/$_{79}$) of these early axSpA patients.

Clinical characteristics (see Table 1) were compared between axSpA that tested positive for antibodies against at least one of the 9 UH-axSpA-IgG peptides and axSpA patients that were seronegative for this panel. As a result, axSpA patients from the UH and (Bio)SPAR cohort combined that showed antibody reactivity against at least one of the 9 targets were significantly older compared to patients without this combined antibody reactivity (44.2 vs. 40.7 years, p=0.0330). Moreover, the percentage of early axSpA patients of the UH and (Bio)SPAR cohort that were HLA- B27 negative was significantly higher in patients with antibodies against at least one of the 9 UH-axSpA-IgG peptides as compared to patients without this combined antibody reactivity (39% vs. 22%, p=0.0401). No significant association between clinical characteristics and the presence or absence of antibody reactivity against at least one of the 9 targets could be found.

Antibodies Are Specifically Directed to Peptides Displayed on Phage

Figure 1B:
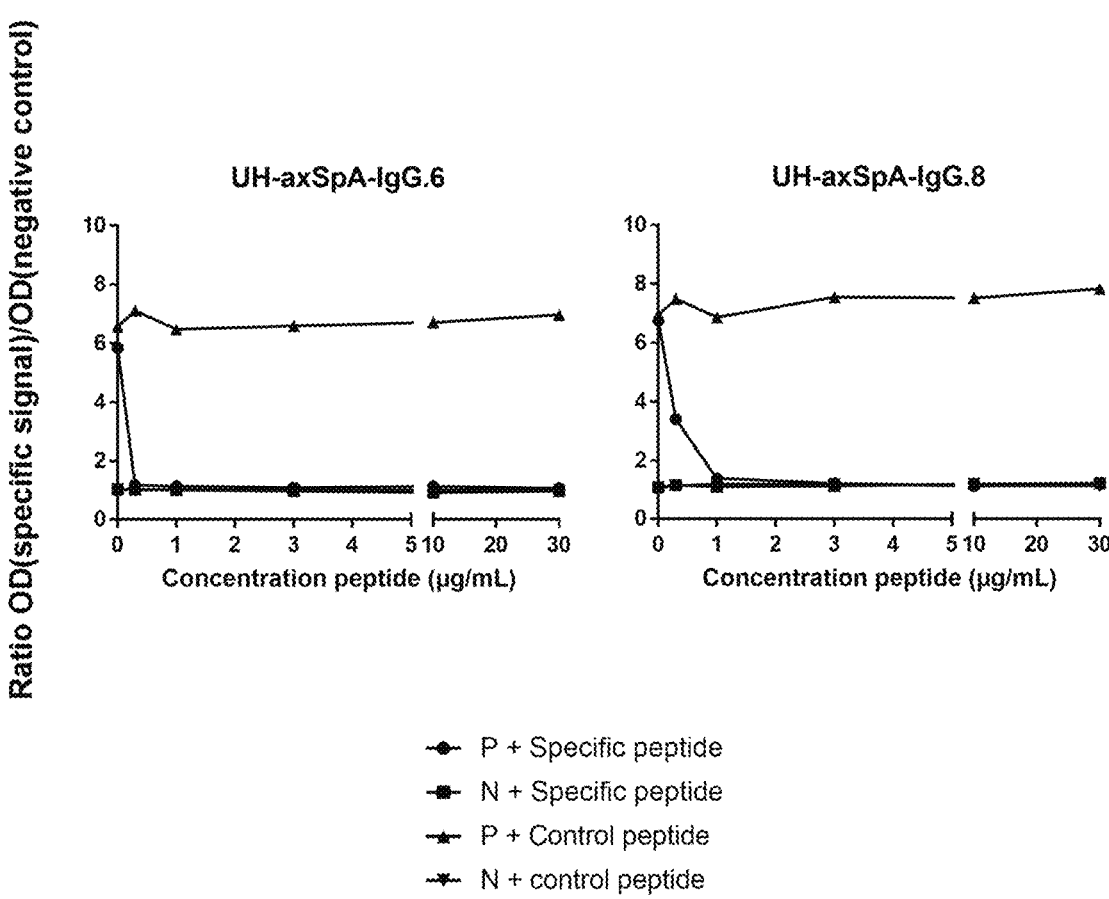

Since antibody reactivity was determined using peptides expressed on the surface of phage particles, a competition ELISA with synthetic peptides was used to investigate the specificity of this interaction. For all six synthetic peptides tested, successful competition between antibodies binding to the synthetic peptide and their corresponding phage-displayed peptide was demonstrated (FIGS. 1A-1B). Even though UH-axSpA-IgG.8 displayed a peptide of 251 aa, a synthetic peptide only of the first 31 aa, corresponding to the C-terminal part of DUX4, was sufficient for full competition.

Expression of Autoantibody Target DUX4 in axSpA Synovial Tissue

To investigate the possible biological relevance of autoantibodies targeting UH-axSpA-IgG.8, representing the C-terminal part of DUX4 in axSpA etiology, expression of DUX4 in synovial axSpA tissue was determined by immunohistochemistry. To our knowledge, presence of the DUX4 protein had not yet been described in synovial tissue. We showed DUX4 expression in walls of blood vessels, but also in separate cells in the connective tissue underlying the synovial lining layer of an axSpA patient (data not shown).

Novel Autoantibodies Are of Added Value for Early axSpA Diagnosis

We explored whether a combination of antibodies against particular peptides could be of added value in discriminating axSpA patients from persons with LBP. By combining UH-axSpA-IgG.1, UH-axSpA-IgG.4 and UH-axSpA-IgG.8, the three peptides with the highest LR+, presence of antibodies against this panel was 14.2% ($^{22}$/$_{155}$) in early axSpA patients from the combined UH and (Bio)SPAR cohorts and only 5% ($^4$/$_{75}$) in persons with LBP (p=0.0484), resulting in a LR+ of 2.7 (Table 4). Disease characteristics did not significantly differ between axSpA patients with antibody reactivity against at least one of the 3 UH-axSpA-IgG peptides compared to patients without this combined antibody reactivity. Assuming a 5% prevalence of axSpA in persons with LBP (pretest probability), combining the presence of inflammatory back pain (LR+3.1) with a positive test result for the laboratory markers HLA-B27 (LR+9.0) and CRP (LR+2.5) (21), resulted in a disease (posttest) probability of 79%. After addition of a positive test result for the presence of autoantibodies to the 3 UH-axSpA-IgG peptides (LR+2.7), posttest probability could be further increased to 91%. On the other hand, a combination of presence of inflammatory back pain (LR+3.1) with a positive test result for CRP (LR+2.5) provided a posttest probability of 27% in case of a negative test result for HLA-B27 (LR–0.9) (21). Addition of a positive test result for the presence of autoantibodies to the 3 UH-axSpA-IgG peptides (LR+2.7) increased the posttest probability to 49%. Results are displayed in Table 5.

Presence of IgM and IgA Antibodies to UH-axSpA-IgG.8

Figure 2A:
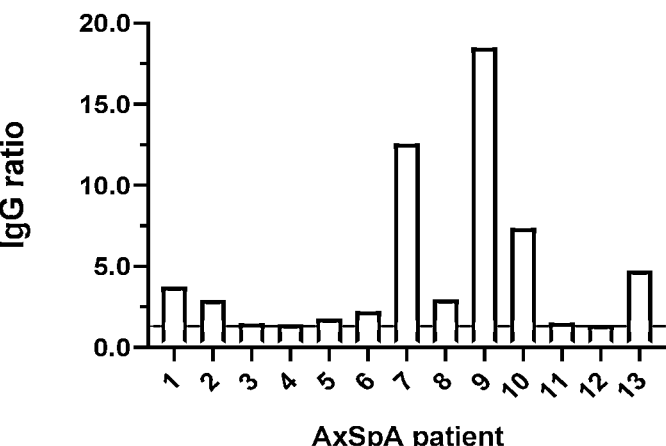
FIGS. 2A-2C Presence of IgM and IgA antibodies in IgG positive patients against UH-axSpA-IgG.8. The presence of IgG (FIG. 2A), IgA (FIG. 2B) and IgM (FIG. 2C) antibodies against UH-axSpA-IgG.8 was measured using a peptide ELISA. Bars represent the ratio of the antibody isotype for each axSpA patient. A patient is considered positive for the indicated antibody isotype when the ratio exceeds 1.3 (solid line).
Figure 2B:
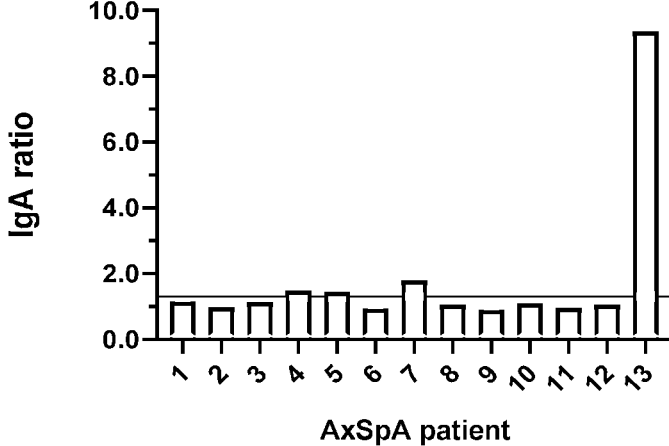
Figure 2C:
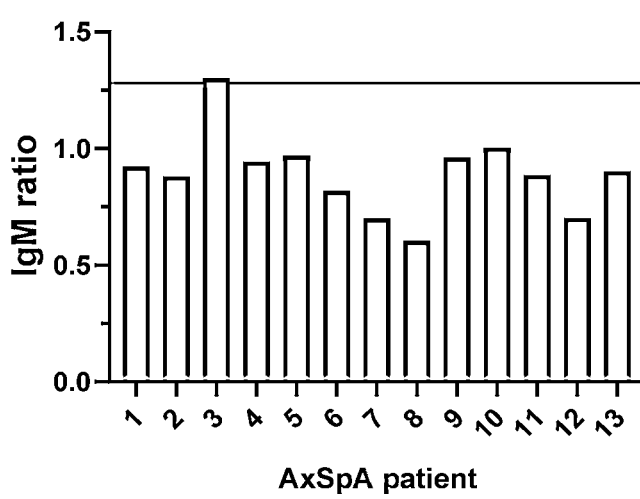

The presence of IgA and IgM antibodies to UH-axSpA-IgG.8 was investigated in 13 IgG antibody positive axSpA patients from the UH and the (Bio)SPAR cohort using the UH-axSpA-IgG.8 peptide ELISA. Of these 13 axSpA patients, antibodies of the IgA and IgM isotype could be detected in 4 and 1 patient(s), respectively (FIGS. 2A-2C).

Presence of Antibodies to UH-axSpA-IgG.8 Could Be Indicative for Therapy Response In a next step, we investigated whether presence of antibodies to UH-axSpA-IgG.8 is indicative for therapy response using the UH-axSpA-IgG.8 peptide ELISA. Therefore, we assessed changes in serology in a longitudinal setting and evaluated whether alterations in antibody status were related to clinical disease activity, indicated by the Bath Ankylosing Spondylitis Disease Activity Index (BAS-DAI). More precisely, antibody reactivity was determined after a 12-months' follow-up period in samples from patients, who tested positive for IgG antibodies against UH-axSpA-IgG.8 (n=8 patients) at baseline.

Figure 3A:
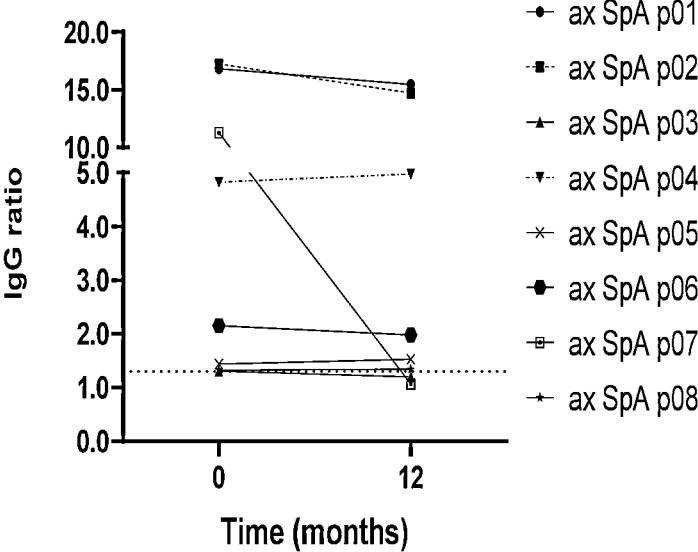
FIGS. 3A-3B Change of antibody reactivity to UH-axSpA-IgG.8 during follow-up in relation to BASDAI score. Antibody reactivity to UH-axSpA-IgG.8 was measured in 8 axSpA patients (axSpA p) at baseline and after a follow up period of 12 months (FIG. 3A).
Figure 3B:
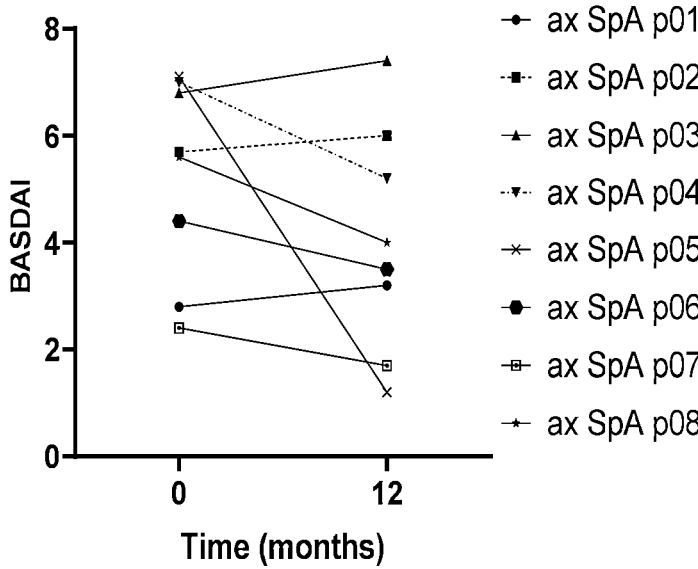

For antibody reactivity towards peptide UH-axSpA-IgG.8, a change from positive (above cut-off 1.3) to negative status (below cut-off 1.3) was observed for two axSpA patients: axSpA p03 and axSpA p07, which was associated with a small increase and decrease in disease activity, respectively. Patient p03 was treated with a biological Disease-Modifying Anti-Rheumatic Drug (bDMARD), whereas patient p07 was treated with a conventional Disease-Modifying Anti-Rheumatic Drug (cDMARD). Interestingly, we observed that 3 patients (namely ax SpA p01, p02 and p04) with high antibody reactivity at baseline and at 12 months' follow-up remain high on BASDAI score upon treatment with a bDMARD (FIGS. 3A-3B).

Although fluctuations in antibody reactivity over time could be observed in relation to disease activity, the predictive effect of IgG antibodies to UH-axSpA-IgG.8 for therapy response should be further investigated in more patients.

TABLE 1

Characteristics of the axSpA patients

| Characteristics | axSpA UHasselt cohort[a] (n = 76) | axSpA (Bio)SPAR cohort Total[b] (n = 174) | Early[d] (n = 79) |
|---|---|---|---|
| Age (mean, SD) | 43.2 (12.7) | 41.9 (12.8) | 36.4 (11.7) |
| Male (n, %) | 43 (56.6) | 115 (66.1) | 48 (60.8) |
| HLA-B27 positive (n, %) | 43 (58.9) | 124 (86.1) | 55 (83.3) |

TABLE 1-continued

Characteristics of the axSpA patients

| Characteristics | axSpA UHasselt cohort[a] (n = 76) | axSpA (Bio)SPAR cohort Total[b] (n = 174) | Early[d] (n = 79) |
|---|---|---|---|
| Disease duration in years[e] (mean, SD) | 2.8 (1.4) | 10.4 (10.9) | 1.4 (1.7) |
| Untreated (n, %) | 11 (14.5) | 13 (7.5) | 5 (6.3) |
| NSAID use (n, %) | 54 (71.1) | 78 (70.3) | 48 (77.4) |
| cDMARD use (n, %) | 30 (39.5) | 24 (21.6) | 15 (24.2) |
| bDMARD (TNFi) use (n, %) | 18 (23.7) | 93 (53.4) | 30 (38.0) |
| BASDAI (mean, SD) | 4.7 (2.1) | 4.4 (2.2) | 3.9 (2.2) |
| BASDAI >4 (n, %) | 31 (55.4) | 58 (54.2) | 27 (45.0) |
| BASFI (mean, SD) | 4.3 (2.6) | 3.6 (2.8) | 2.8 (2.4) |
| ESR, mm/h (mean, SD) | 11.5 (15.2) | 19.1 (21.6) | 19.3 (21.9) |
| ESR >20 mm/h (n, %) | 9 (13.6) | 53 (31.4) | 23 (30.7) |
| CRP, mg/L (median, IQR) | 2.5 (0.7-7.8) | 4.3 (1.3-12.8) | 5.3 (1.2-15.6) |
| CRP >5 mg/L (n, %) | 23 (33.8) | 80 (47.3) | 39 (51.3) |
| Extra-articular manifestations (n, %) | 15 (19.7) | 34 (21.9) | 17 (25.0) |
| Involvement peripheral joints (n, %) | 23 (30.3) | 17 (25.4) | 6 (20.0) |
| Positive family history of SpA (n, %) | 37 (66.1) | 75 (50.7) | 33 (47.8) |

[a]For axSpA patients in the UHasselt cohort, missing values were below 10% except for BASDAI (26.3%), BASFI (27.6%), ESR (13.2%), CRP (10.5%) and positive family history of SpA (26.3%).
[b]Within the total (Bio)SPAR cohort, missing values were also below 10%, except for HLA-B27 status (17.2%), NSAID use (36.2%), cDMARD use (36.2%), BASDAI (38.5%), BASFI (39.1%), extra-articular manifestations (10.9%), involvement peripheral joints (61.5%) and positive family history of SpA (14.9%).
[d]Missing values for axSpA patients in the early (Bio)SPAR cohort were below 10%, except for HLA-B27 (16.5%), NSAID use (21.5%), cDMARD use (21.5%), BASDAI (24.1%), BASFI (22.8%), extra-articular manifestations (13.9%), involvement peripheral joints (62.0%) and positive family history of SpA (12.7%).
[e]Disease duration, time between diagnosis and blood sampling
HLA-B27, Human Leukocyte Antigen-B27;
NSAID, Non-Steroidal Anti-Inflammatory Drugs;
cDMARD, conventional Disease Modifying Antirheumatic Drugs;
bDMARD, biological Disease-Modifying Anti-Rheumatic Drugs;
TNFi, Tumor Necrosis Factor inhibitors;
BASDAI, Bath Ankylosing Spondylitis Disease Activity Index;
BASFI, Bath Ankylosing Spondylitis Functional Index;
ESR, Erythrocyte Sedimentation Rate;
CRP, C-Reactive Protein.

TABLE 2

Identity of 9 novel antigens targeted by antibody responses in early axSpA patients

| Antibody targets | cDNA identity (NCBI Accession No.) | Fusion type[b], frame | Peptide sequence of cDNA insert[c] | Size (aa)[d] | Homology on amino acid level (UniProt Accession No.) |
|---|---|---|---|---|---|
| UH-axSpA-IgG.1 | Tubulin gamma complex associated protein 2 (NM_001256617.1) | mRNA, coding, No | (IP)GPAEHLQHQ* | 11 | 8/10 (80%) Eukaryotic translation initiation factor 4E type 2, EIF4E2 (O60573)<br>6/6 (100%) Adenylate cyclase type 8, ADCY8 (P40145)<br>8/13 (62%) Cyclic AMP-responsive element-binding protein 3-like protein, CREB3L4 (Q8TEY5) |
| UH-axSpA-IgG.2 | RNA polymerase II associated protein 2 (NM_024813.3) | RNA, 3'UTR | (WA)PTSKTKDR* | 10 | 7/7 (100%) 1-phosphatidylinositol 4,5-biphosphate phosphodiesterase gamma-2, PLCG2 (P16885)<br>7/10 (70%) WD repeat-containing and planar cell polarity effector protein fritz homolog, WDPCP (O95876)<br>6/6 (100%) G patch domain-containing protein 1, GPATCH1 (Q9BRR8) |
| UH-axSpA-IgG.3 | Predicted: MAM domain containing glycosylphosphatidylinositol anchor 1 (XR_926140.2) | RNA | (WG)QAELMNKNGV GQKILHPLGLPNHLH RSFCPWLGLDFIRSF FWGR* | 46 | 7/9 (78%) D-amino acid oxidase activator, DAOA (P59103)<br>10/14 (71%) Autism susceptibility gene 2 protein, AUTS2 (Q8WXX7)<br>7/10 (70%) Leucine-rich repeat and IQ domain-containing protein 3, LRRIQ3 (A6PVS8) |
| UH-axSpA-IgG.4 | PREDICTED: Uncharacterized LOC105379031 (XR_953469.2) | ncRNA | (IP)ELLLWKIQP* | 11 | 6/7 (86%) G-protein coupled receptor 37-like 1 precursor, GPR37L1 (O60883)<br>6/9 (67%) 2-methoxy-6-polyprenyl-1,4-benzoquinol methylase, COQ5 (Q5HYK3)<br>6/7 (86%) Rap guanine nucleotide exchange factor 1, RAPGEF1 (Q13905) |
| UH-axSpA-IgG.5 | MAGE family member D4 (NM_001272063.2) | mRNA, coding, No | (IP)ISTF* | 6 | 5/5 (100%) Mucin-16, MUC16 (Q8WXI7)<br>5/6 (83%) Activating transcription factor 7-interacting protein 1, ATF7IP (Q6VMQ6)<br>5/5 (100%) F-box only protein 47, FBXO47 (Q5MNV8) |
| UH-axSpA-IgG.6 | Malate dehydrogenase 2 (NM_005918.4) | mRNA, coding, No | (IR)QRCSPPQLQHL GPEQC* | 18 | 9/13 (69%) Oxysterols receptor LXR-alpha, NR1H3 (Q13133)<br>9/20 (45%) Transforming acidic coiled-coil-containing protein 2, TACC2 (O95359)<br>7/10 (70%) Histone-lysine N-methyltransferase 2D, KMT2D (O14686) |
| UH-axSpA-IgG.7 | Death associated protein 3 (NM_033657.2) | mRNA, coding, No | (WA)ESYFPHQ* | 9 | 6/6 (100%) Intraflagellar transport protein 56, TTC26 (A0AVF1)<br>8/15 (53%) Integrator complex subunit 10, INTS10 (Q9NVR2)<br>5/5 (100%) TRAF3-interacting JNK-activating modulator, TRAF3IP3 (Q9Y228) |
| UH-axSpA-IgG.8 | Double homeobox protein 4 (NM_001306068.2) | mRNA, coding, Yes | (IP)PGELEALEGATS LEAPLSEEEYRALLE ELQDARLGRGRLRA GRWPLFRREHLAGY VGSCLPHATSTGLTS LGFLPSRSRPPGERL HTAETPHSGELPFFP | 252 | 26/29 (90%) Double homeobox protein 4-like, DUX4 (Q9UBX2)<br>21/47 (45%) 26S proteasome non-ATPase regulatory subunit 5, PSMD5 (Q16401)<br>21/45 (47%) Phosphatidylinositol 4,5-bisphosphate 5-phosphatase A, INPP5J (Q15735) |

TABLE 2-continued

Identity of 9 novel antigens targeted by antibody responses in early axSpA patients

| Antibody targets | cDNA identity (NCBI Accession No.) | Fusion type[a], in frame[b] | Peptide sequence of cDNA insert[c] | Size (aa)[d] | Homology on amino acid level (UniProt Accession No.) |
|---|---|---|---|---|---|
| | | | GHPGASRLGQRPDA LHLPLPCGGFRGHG LARWSCPGFQFARC PGDLGSPDPAPPRT PLGSGWCKHTLALC PHLSGPRLSHSARA RQAVALQVPVLPAF PQVQRPPRSLRVGE SPFQRSRGGVGKIP TCRGRLGHPRCRCG LAGLEGTAAAN* | | |
| UH-axSpA-IgG.9 | 28S ribosomal RNA (NR_146154.1) | Ribosomal RNA | (LG)ARTKAAVAQ* | 11 | 7/9 (78%) FRAS1-related extracellular matrix protein 1, FREM1 (Q5H8C1) 6/8 (75%) Transmembrane and coiled-coil domains protein 1, TMCC1 (O94876) 6/7 (86%) RIMS-binding protein 2, RIMBP2 (O15034) |

[a]Origin of the cDNA insert of the phage-displayed target
[b]In-frame fusion of the cDNA insert with the M13 gene VI: Yes/No. Translation of in-frame fusion results in expression of (part of) a human protein, whereas out-of-frame fusion results in a fusion construct with a random peptide sequence.
[c]Peptide sequence of the translated cDNA insert, with the first aa between parenthesis representing the last full aa of the adaptor sequence and the second aa between parenthesis representing the aa formed by the fusion between the adaptor and the cDNA insert.
the transition between the M13 phagemid vector and the cDNA insert.
[d]Size of translated cDNA insert in aa
QAmber stop codon, which is translated into glutamine by the bacterial strain
*stop codon
UTR, untranslated region,
mRNA, messenger RNA,
ncRNA, non-coding RNA

TABLE 3

Presence of antibodies against UH-axSpA-IgG.1-9 in axSpA patients and controls

| | UHasselt | (Bio)SPAR registry | | | | |
| | cohort | Total | Early | | Controls | |
| Antibody targets | axSpA (n = 76) | axSpA (n = 174) | axSpA (n = 79) | HC (n = 94) | LBP (n = 75) | RA (n = 60) |
| --- | --- | --- | --- | --- | --- | --- |
| UH-axSpA-IgG.1 | 2/76 (3%) | 6/174 (3%) | 3/79 (4%) | 1/94 (1%) | 1/75 (1%) | 0/60 (0%) |
| UH-axSpA-IgG.2 | 3/76 (4%) | 4/174 (2%) | 1/79 (1%) | 2/94 (2%) | 2/75 (3%) | 1/60 (2%) |
| UH-axSpA-IgG.3 | 5/76 (7%) | 8/174 (5%) | 5/79 (6%) | 2/94 (2%) | 3/75 (4%) | 1/60 (2%) |
| UH-axSpA-IgG.4 | 6/76 (8%) | 5/174 (3%) | 3/79 (4%) | 4/94 (4%) | 0/75 (0%) | 2/60 (3%) |
| UH-axSpA-IgG.5 | 10/76 (13%) | 32/174 (18%) | 8/79 (10%) | 6/94 (6%) | 12/75 (16%) | 6/60 (10%) |
| UH-axSpA-IgG.6 | 6/76 (8%) | 8/174 (5%) | 4/79 (5%) | 4/94 (4%) | 3/75 (4%) | 3/60 (5%) |
| UH-axSpA-IgG.7 | 2/76 (3%) | 5/174 (3%) | 1/79 (1%) | 3/94 (3%) | 4/75 (5%) | 4/60 (7%) |
| UH-axSpA-IgG.8 | 4/76 (5%) | 14/174 (8%) | 6/79 (8%) | 3/94 (3%) | 3/75 (4%) | 4/60 (7%) |
| UH-axSpA-IgG.9 | 7/76 (9%) | 12/174 (7%) | 4/79 (5%) | 5/94 (5%) | 5/75 (7%) | 7/60 (12%) |
| At least one of 9 peptides | 41/76 (54%) | 74/174 (43%) | 27/79 (34%) | 24/94 (26%) | 29/75 (39%) | 23/60 (38%) |

20

TABLE 4

Presence of antibodies against particular UH-axSpA-IgG.1-9 peptides, at least one of
the 9 peptides and our panel of 3 peptides in axSpA patients compared to persons with LBP

| | LBP (n = 75) | All axSpA (n = 250) | | | Early axSpA (n = 155) | | |
| Antibody targets | Spec (%) | Sens (%) | P value | LR+ | Sens (%) | P value | LR+ |
| --- | --- | --- | --- | --- | --- | --- | --- |
| UH-axSpA-IgG.1 | 1/75 (99%) | 8/250 (3%) | 0.6903 | 3.0 | 5/155 (3%) | 0.6666 | 3.0 |
| UH-axSpA-IgG.2 | 2/75 (97%) | 7/250 (3%) | 1.0000 | 1.0 | 4/155 (3%) | 1.0000 | 1.0 |
| UH-axSpA-IgG.3 | 3/75 (96%) | 13/250 (5%) | 1.0000 | 1.25 | 10/155 (6%) | 0.5546 | 1.5 |
| UH-axSpA-IgG.4 | 0/75 (100%) | 11/250 (4%) | 0.0744 | — | 9/155 (6%) | 0.0328 | — |
| UH-axSpA-IgG.5 | 12/75 (84%) | 42/250 (17%) | 1.0000 | 1.1 | 18/155 (12%) | 0.4048 | 0.75 |
| UH-axSpA-IgG.6 | 3/75 (96%) | 14/250 (6%) | 0.7710 | 1.5 | 10/155 (6%) | 0.5546 | 1.5 |
| UH-axSpA-IgG.7 | 4/75 (95%) | 7/250 (3%) | 0.2854 | 0.6 | 3/155 (2%) | 0.2192 | 0.4 |
| UH-axSpA-IgG.8 | 3/75 (96%) | 18/250 (7%) | 0.4278 | 1.75 | 10/155 (6%) | 0.5546 | 1.5 |
| UH-axSpA-IgG.9 | 5/75 (93%) | 19/250 (8%) | 1.0000 | 1.1 | 11/155 (7%) | 1.0000 | 1.0 |
| At least one of 9 peptides | 29/75 (61%) | 115/250 (46%) | 0.2904 | 1.1 | 68/155 (44%) | 0.4793 | 1.1 |
| Panel of 3 peptides (bold) | 4/75 (95%) | 34/250 (13.6%) | 0.0637 | 2.55 | 22/155 (14.2%) | 0.0484 | 2.66 |

TABLE 5

Added value of antibody panel to axSpA posttest probability

| Test combination | axSpA Posttest probability |
| --- | --- |
| HLA-B27 pos (LR + 9.0), inflammatory back pain (LR + 3.1), CRP (LR + 2.5) (21) | 79% |
| HLA-B27 pos (LR + 9.0), inflammatory back pain (LR + 3.1), CRP (LR + 2.5) + panel 3 UH-axSpA Abs (LR + 2.7) | 91% |
| HLA-B27 neg (LR − 0.9), inflammatory back pain (LR + 3.1), CRP (LR + 2.5) (21) | 27% |
| HLA-B27 neg (LR − 0.9), inflammatory back pain (LR + 3.1), CRP (LR + 2.5) + panel 3 UH-axSpA Abs (LR + 2.7) | 49% |

REFERENCES

1. Sieper J, Poddubnyy D. Axial spondyloarthritis. Lancet. 2017;390(10089):73-84.

2. Rudwaleit M, Landewe R, van der Heijde D, Listing J, Brandt J, Braun J, et al. The development of Assessment of SpondyloArthritis international Society classification criteria for axial spondyloarthritis (part I): classification of paper patients by expert opinion including uncertainty appraisal. Ann Rheum Dis. 2009;68(6):770-6.

3. Rudwaleit M, van der Heijde D, Landewe R, Listing J, Akkoc N, Brandt J, et al. The development of Assessment of SpondyloArthritis international Society classification criteria for axial spondyloarthritis (part II): validation and final selection. Ann Rheum Dis. 2009;68(6):777-83.

4. de Vlam K. Soluble and tissue biomarkers in ankylosing spondylitis. Best Pract Res Clin Rheumatol. 2010;24(5):671-82.

5. de Winter J, de Hooge M, van de Sande M, de Jong H, van Hoeven L, de Koning A, et al. Magnetic Resonance Imaging of the Sacroiliac Joints Indicating Sacroiliitis According to the Assessment of SpondyloArthritis international Society Definition in Healthy Individuals, Runners, and Women With Postpartum Back Pain. Arthritis Rheumatol. 2018;70 (7):1042-8.

6. Ez-Zaitouni Z, Landewe R, van Lunteren M, Bakker P A, Fagerli K M, Ramonda R, et al. Imaging of the sacroiliac joints is important for diagnosing early axial spondyloarthritis but not all-decisive. Rheumatology (Oxford). 2018.

7. Dincer U, Cakar E, Kiralp M Z, Dursun H. Diagnosis delay in patients with ankylosing spondylitis: possible reasons and proposals for new diagnostic criteria. Clin Rheumatol. 2008;27(4):457-62.

8. Masson Behar V, Dougados M, Etcheto A, Kreis S, Fabre S, Hudry C, et al. Diagnostic delay in axial spondyloarthritis: A cross-sectional study of 432 patients. Joint Bone Spine. 2017;84(4):467-71.

9. Quaden D H, De Winter L M, Somers V. Detection of novel diagnostic antibodies in ankylosing spondylitis: An overview. Autoimmun Rev. 2016;15(8):820-32.

10. Hague N, Lories R J, de Vlam K. Orthopaedic interventions in patients with psoriatic arthritis: a descriptive report from the SPAR cohort. RMD Open. 2016;2(2):e000293.

11. Westhovens I, Lories R J, Westhovens R, Verschueren P, de Vlam K. Anti-TNF therapy and malignancy in spondyloarthritis in the Leuven spondyloarthritis biologics cohort (BIOSPAR). Clin Exp Rheumatol. 2014;32(1):71-6.

12. Arnett F C, Edworthy S M, Bloch D A, McShane D J, Fries J F, Cooper N S, et al. The American Rheumatism Association 1987 revised criteria for the classification of rheumatoid arthritis. Arthritis Rheum. 1988;31(3):315-24.

13. Airaksinen O, Brox J I, Cedraschi C, Hildebrandt J, Klaber-Moffett J, Kovacs F, et al. Chapter 4. European guidelines for the management of chronic nonspecific low back pain. Eur Spine J. 2006;15 Suppl 2:S192-300.

14. Vandormael P, Verschueren P, De Winter L, Somers V. cDNA phage display for the discovery of theranostic autoantibodies in rheumatoid arthritis. Immunol Res. 2017;65(1):307-25.

15. Hufton S E, Moerkerk P T, Meulemans E V, de Bruine A, Arends J W, Hoogenboom H R. Phage display of cDNA repertoires: the pVI display system and its applications for the selection of immunogenic ligands. J Immunol Methods. 1999;231(1-2):39-51.

16. Somers K, Geusens P, Elewaut D, De Keyser F, Rummens J L, Coenen M, et al. Novel autoantibody markers for early and seronegative rheumatoid arthritis. J Autoimmun. 2011 ;36(1):33-46.

17. Somers K, Stinissen P, Somers V. Optimization of high-throughput autoantibody profiling for the discovery of novel antigenic targets in rheumatoid arthritis. Ann N Y Acad Sci. 2009;1173:92-102.

18. Somers V, Govarts C, Hellings N, Hupperts R, Stinissen P. Profiling the autoantibody repertoire by serological antigen selection. J Autoimmun. 2005;25(3):223-8.

19. Somers V, Govarts C, Somers K, Hupperts R, Medaer R, Stinissen P. Autoantibody profiling in multiple sclerosis reveals novel antigenic candidates. J Immunol. 2008;180(6):3957-63.

20. Rudwaleit M, Khan M A, Sieper J. The challenge of diagnosis and classification in early ankylosing spondylitis: do we need new criteria? Arthritis Rheum. 2005;52(4):1000-8.

21. Rudwaleit M, van der Heijde D, Khan M A, Braun J, Sieper J. How to diagnose axial spondyloarthritis early. Ann Rheum Dis. 2004;63(5):535-43.

The invention claimed is:

1. An in vitro method comprising:

detecting the presence or quantity of autoantibodies in a sample of a subject wherein the autoantibodies bind to a polypeptide comprising the full-length of SEQ ID No: 8;

wherein the subject is a human subject suspected of having spondyloarthritis or wherein the human subject has spondyloarthritis, and wherein the sample is a blood serum sample or blood plasma sample.

2. The in vitro method according to claim 1, further comprising detecting the presence or quantity of autoantibodies in the sample of the subject wherein the autoantibodies bind to a second polypeptide comprising the full length of a sequence selected from the list comprising SEQ ID No: 1, SEQ ID No: 2, SEQ ID No: 3, SEQ ID No: 4, SEQ ID No: 5, SEQ ID No: 6, SEQ ID No: 7, SEQ ID No: 9.

3. The in vitro method according to claim 1, further comprising detecting the presence or quantity of autoantibodies in the sample of the subject wherein the autoantibodies bind to one or more additional polypeptides comprising the full length of a sequence selected from SEQ ID No. 1 and SEQ ID No. 4.

4. The in vitro method according to claim 1, further comprising:

detecting the presence or quantity of autoantibodies in the sample, wherein the autoantibodies bind to polypeptides comprising the full length sequence of SEQ ID No: 1 and SEQ ID No: 4.

5. The in vitro method of claim 1, wherein the presence or quantity of autoantibodies that bind to a polypeptide comprising a full-length sequence of SEQ ID NO: 11 are detected.

* * * * *